United States Patent
Zhou et al.

(10) Patent No.: US 9,732,097 B2
(45) Date of Patent: Aug. 15, 2017

(54) PROCESS FOR THE SYNTHESIS OF A PHOSPHOINOSITIDE 3-KINASE INHIBITOR

(71) Applicant: Incyte Corporation, Wilmington, DE (US)

(72) Inventors: Jiacheng Zhou, Newark, DE (US); Lei Qiao, Downingtown, PA (US); Lingkai Weng, Malvern, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/151,050

(22) Filed: May 10, 2016

(65) Prior Publication Data

US 2016/0362426 A1    Dec. 15, 2016

Related U.S. Application Data

(60) Provisional application No. 62/159,674, filed on May 11, 2015.

(51) Int. Cl.
*C07D 473/34* (2006.01)
*C07D 519/00* (2006.01)
*C07D 473/40* (2006.01)
*C07D 513/04* (2006.01)

(52) U.S. Cl.
CPC ......... *C07D 519/00* (2013.01); *C07D 473/34* (2013.01); *C07D 473/40* (2013.01); *C07D 513/04* (2013.01)

(58) Field of Classification Search
None
See application file for complete search history.

(56) References Cited

U.S. PATENT DOCUMENTS

| | | |
|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmerman |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | McKew et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopt et al. |
| 7,528,143 B2 | 5/2009 | Noronha et al. |
| 7,598,257 B2 | 10/2009 | Rodgers et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 9,249,087 B2 | 2/2016 | Kozikowski et al. |
| 9,434,746 B2 | 9/2016 | Li et al. |
| 2003/0008898 A1 | 1/2003 | Mahhoobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

"A to Z List of Cancers," National Cancer Institute (http://www.cancer.gov/) (Downloaded May 29, 2014), 22 pages.
"Angiogenesis" Merriam-Webster.com. Merriam-Webster, n.d. Web Jun. 16, 2014, www.merriam-webster.com/dictionary/angiogenesis, 3 pages.
"Arthritis: MedlinePlus Medical Encyclopedica," 2014, p. 1-5, accessed online Oct. 7, 2014; http://www.nlm.nib.gove/medlineplus/ency/article/001243.htm.
"Autoimmune disorders: MedlinePlus Medical Encyclopedia," 2013, p. 1-4, accessed online Oct. 7, 2014; http://www.nlm.nih.gov/medlineplus/ency/article/000816.htm.
"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

(Continued)

*Primary Examiner* — Golam M M Shameem
*Assistant Examiner* — Laura Daniel
(74) *Attorney, Agent, or Firm* — Fish & Richardson P.C.

(57) ABSTRACT

The present application is directed to processes and intermediates for making (S)-7-(1-((9H-purin-6-yl)amino)ethyl)-6-(3-fluorophenyl)-3-methyl-5H-thiazolo[3,2-a]pyrimidin-5-one, which is an inhibitor of phosphoinositide 3-kinases (PI3Ks), useful in the treatment of diseases related to the activity of PI3Ks including, for example, inflammatory disorders, immune-based disorders, cancer, and other diseases.

39 Claims, No Drawings

(56) References Cited

U.S. PATENT DOCUMENTS

| | | |
|---|---|---|
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto et al. |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121198 A1 | 5/2014 | Li et al. |
| 2014/0121222 A1 | 5/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361094 A1 | 12/2015 | Li et al. |
| 2016/0022685 A1 | 1/2016 | Li et al. |
| 2016/0024117 A1 | 1/2016 | Li et al. |
| 2016/0257689 A1 | 9/2016 | Qiao et al. |
| 2016/0264580 A1 | 9/2016 | Combs et al. |
| 2016/0362424 A1 | 12/2016 | Li et al. |
| 2016/0362425 A1 | 12/2016 | Li et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 93/16076 | 8/1993 |
| WO | WO 93/22291 | 11/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |

(56) References Cited

FOREIGN PATENT DOCUMENTS

| | | |
|---|---|---|
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/026701 | 3/2009 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/052699 | 4/2013 |
| WO | WO 2013052699 A3 * | 6/2013 ........... C07D 473/16 |
| WO | WO 2013/151930 | 10/2013 |

OTHER PUBLICATIONS

Ali, et al., "Essential role for the p110δ phosphoinositide 3-kinase in the allergic response," Nature. 2004, 431(7011):1007-11.

Allen, et al., "Synthesis of C-6 substituted pyrazolo [1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11): 691-699.

Bader, et al., "Cancer-specific mutations in PIK3CA are oncogenic in vivo," Proc Natl Acad Sci U S A. 2006, 103(5):1475-9.

Baek et al., "Complete remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-1199.

Barber, et al., "PI3Kγ inhibition blocks glomerulonephritis and extends lifespan in a mouse model of systemic lupus," Nat Med. 2005, 11(9):933-5.

Barragan et al., "Protein Kinases in the Regulation of Apoptosis in B-cell Chronic Lymphocytic Leukemia," *Leukemia and Lymphoma*, 2003, 44(11):1865-1870.

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

Bendell, J.C., "Phase I, dose-escalation study of BKM120, an oral pan-Class I PI3K inhibitor, in patients with advanced solid tumors," Journal of Clincial Oncology (2011): JCO-2011.

Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.

Bennasar, et al., "Generation and Intermolecular Reactions of 2-Indolylacyl Radicals," *Organic Letters* (2001), 3(11), 1697-1700, CODEN: ORLEF7; ISSN: 1523-7060.

Berge et al., "Pharmaceutical Salts," J Pharma Sci, 1977, 66(1):1-19.

Bergman, et al., "Synthesis of indolocarbazole quinones; potent aryl hydrocarbon receptor ligands," *Tetrahedron* (2002), 58(7), 1443-1452.

Bhatia and Rose, "Autoimmunity and autoimmune disease," Principles of Med Biol., 1996, 6:239-263, 244.

(56) References Cited

OTHER PUBLICATIONS

Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Blom et al., "Two-Pump at col. Dilution Configuration for Preparative LC-MS," 2002, 4: 295.
Blom et al., "Optimizing Preparative LC-MS Configurations and Methods for Parallel Synthesis Purification," 2003, 5: 670.
Boger, et al., "First and Second Generation Total Synthesis of the Teicoplanin Aglycon," JACS, 123(9), 1862-1871, 2001.
Brachmann et al., "PI3K and mTOR inhibitors—a new generation of targeted anticancer agents," Current Opinion Cell Biol., 2009, 21:194-198.
Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," *Bioorganic & Medicinal Chemistry Letters* (2006), 16(17), 4697-4699.
Cacoub et al., "Anti-CD20 monoclonal antibody (rituximab) treatment for cryoglobulinemic vasculitis: where do we stand?," Ann Rheum Dis, Mar. 2008, 67: 283-287.
Camps, et al., "Blockade of PI3Kγ suppresses joint inflammation and damage in mouse models of rheumatoid arthritis," Nat Med. 2005, 11(9):936-43.
Cannon, Burger's Medicinal Chemistry and Drug Discovery, Fifth Edition, vol. 1 Principles and Practice, Wiley-Interscience 1995, Ch. 19, pp, 783-803, 784.
Cantley, "The Phosphoinositide 3-Kinase Pathway," Science, (2002) 296 (5573):1655-7.
Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.
Chai, a al., "Synthesis and in vitro anti-hepatitis B virus activities of some ethyl 6-bromo-5-hydroxy-1H-indole-3-carboxylates," *Bioorganic & Medicinal Chemistry* (2006), 14(4), 911-917.
Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.
Chen, X., "Targeting oxidative stress in embryonal rhabdomyosarcoma," Cancer cell 24.6 (2013): 710-724.
Clayton, et al., "A Crucial Role for the p110δ Subunit of Phosphatidylinositol 3-Kinase in B Cell Development and Activation," J Exp Med. 2002, 196(6):753-63.
Collins et al., "Rituximab treatment of fibrillary glomerulonephritis," Am J Kidney Dis., 2008, 52(6):1158-62.
Coughlin et al., Approaches and limitations of phosphatidylinositol-3-kinase pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Crabbe, "The PI3K inhibitor arsenal: choose your weapon!" Trends Biochem Sci., 2007, 32(10):450-56.
Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941.
DeBerardinis et al., "The Biology of Cancer: Metabolic Reprogramming Fuels Cell Growth and Proliferation," Cell Metabolism, Jan. 2008, 7:11-20.
Delmas and Meunier, "The Management of Paget's Disease of Bone," N Engl J Med., 1997, 336:558-566.
Devauchelle-Pensec, "Treatment of Primary Sjogren Syndrome with Rituximab," Annal Internal Med., 2014, 160:233-242.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido [2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Cancer, 2009, 9:550-562.
Fadeyeva, et al., "Inhibitors of early virus-cell interaction stages among 3-ethovcarbonyl-5-hydroxy-bromoindole derivatives," *Khimiko-Farmatsevticheskii Zhurnal* (1992), 26(9-10), 17-20 (with English abstract).
Fine et al., "Neoplasms of the Central Nervous System," Cancer Principles Practice Oncol., 2005, 2:1834-1887.
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatography, Biomedical Applications*, (1981), 225(1), 73-81.
Froman and Bismuth, "Fine Tuning the Immune Response with PI3K," *Immunological Revs.*, 2006, 228:253-272.
Garvey, "Rituximab in the treatment of autoimmune haematolgoical disorders," British Journal of Haematology, 2008, 141: 149-169.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Ghigo et al., "PI3K inhibition in inflammation: Toward tailored therapies for specific diseases," BioEssays, 2010, 32:185-196.
Godeau et al., "Rituximab efficacy and safety in adult splenectomy candidates with chronic immune thrombocytopenic purpura: results of a prospective multicenter phase 2 study," Blood, 2008, 112(4): 999-1004.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).

(56) References Cited

OTHER PUBLICATIONS

Greene and P. G. M. Wuts, Protective Groups in Organic Synthesis, 3rd Ed., Wiley & Sons, Inc., New York (1999)*Too Voluminous to Provide.
Wuts and Greene, Protective Groups in Organic Synthesis, 4th ed., John Wiley & Sons: New Jersey, pp. 696-887,2007.
Harley, "Medical Management of Actue Renal Failure," Renal Failure Replacement Therapies, 2008, pp. 26-32.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing—Remitting Multiple Sclerosis," The New England Journal of Medicine, 358(7):676-688, 2008.
Hayter and Cook, "Updated assessment of the prevalence, spectrum and case definition of autoimmune disease," Autoimmunity Reviews, 2012, 11:754-765.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota, "Efficient synthesis of 2,9-disubstituted 8-hydroxyadenine derivatives", Organic & Biomolecular Chemistry (2003), 1(8), 1354-1365.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of a fluorine-containing cytokinin, N6-pentafluoro-benzyladenosine," *Youji Huaxue* (1988), 8(2), 147-8 (with English abstract).
Ihle et al., "Inhibitors of phosphatidylinositol-3-kinase in cancer therapy", *Molecular Aspects of Medicine*, 31(2):135-144, 2010.
Irie, et al., "Discovery of selective and nonpeptidic cathepsin Sinhibitors," *Bioorganic & Medicinal Chemistry Letters* (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie*, International Edition in English (1996), 35(16), 1815-1818.
Japanese Office Action in Japanese Application No. 2014-528654, dated Mar. 29, 2016, 5 pages (English Translation).
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.

Kang et al., "Aplidiamine, a unique zwitterionic benzyl hydroxyadenine from the Western Australian marine ascidian *Aplidiopsis* sp.," *Tetrahedron Letters* (1997), 38(6), 941-944.
Kang, et al., "Phosphtidylinositol 3-kinase mutations identified in human cancer are oncogenic," Proc Natl Acad Sci U S A. 2005, 102(3):802-7.
Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.
Kim et al., "A signaling network in Phenylephrine-Induced Benign Prostatic Hyperplasia," Endocrinology, 2009, 150:3576-3583.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," *Bioorganic & Medicinal Chemistry* (1997), 5(3), 507-514.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 9:1734-1740.
Kong and Yamori, "Advances in Development of Phosphatidylinositol 3-Kinase Inhibitors," Current Medicinal Chemistry, 16:2839-2854, 2009.
Kuduk et al., "Heterocyclic fused pyridone carboxylic acid M1 positive allosteric modulators," *Bioorganic & Medicinal Chemistry Letters* (2010), 20(8), 2533-2537.
Kung et al., "Characterization of a Murine Model of Allergic Pulmonary Inflammation," Int. Arch. Allergy Immunol., (abstract), 105(1):83-90, 1994.
Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.
Kuster (ed), Kinase Inhibitors: Methods and Protocols Methods in Molecular Biology, 2012, 795:1-44.
Kutney, et al., "Dihydropyridines in synthesis and biosynthesis. IV. Dehydrosecodine, in vitro precursor of indole alkaloids," *Canadian Journal of Chemistry* (1982), 60(11), 1269-78.
Lee, et al., "Inhibition of phosphoinositide 3-kinase δ attenuates allergic airway inflammation and hyperresponsiveness in murine asthma model," FASEB J. 2006, 20(3):455-65.
Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).
Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).
Li, et al., "Optimization of the heterocyclic core of the quinazolinone-derived CXCR3 antagonists," *Bioorganic & Medicinal Chemistry Letters* (2008), 18(2), 688-693.

(56) References Cited

OTHER PUBLICATIONS

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lipsky, "Systemic lupus erythematosus: an autoimmune disease of B cell hyperactivity," Nat Immunol., 2001, 2(9):764-6.

Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Strategies, 2009, 6:47-55.

Lovric et al., "Rituximab as rescue therapy in anti-neutrophil cytoplasmic antibody-associated vasculitis: a single-centre expereince with 15 patients," Nephrol Dial Transplant, 2009, 24: 179-185.

Lucas, et al., "Rauwolfia alkaloids. XXXI. The synthesis and activity of some reserpine analogs," *Journal of the American Chemical Society* (1959), 81, 1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga *Rhodomela confervoides*", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

MedicineNet.com' [online]. "Definition of Cancer," Sep. 18, 2004, retrieved on Sep. 16, 2005. Retrieved from the Internet: http://www.medterms.com, 1 page.

Medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#149398?&_suid=14297429843880910545130428968​4>. 10 pages.

Meijer et al., "Treatment of primary Sjögren syndrome with rituximab: extended follow-up, safety and efficacy of retreatment," Ann. Rheum. Dis., 68(2):284-285, 2009.

Medeot et al., "Rituximab therapy in adult patients with relapsed or refractory immune thrombocytopenic purpura: long-term follow-up results," European Journal of Haematology, 2008, 81: 165-169.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Mild, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Mild, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society, Perkin Transactions 1* (2001), (18), 2213-2216.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Najiwara, et al., Generation and behavior of naphthoyloxyl radicals in photocleavage of 1-(naphthoyloxy)-2-pyridones, *Chemistry Letters* (2001), (10), 1064-1065.

Nettekoven, M., "A combinatorial approach towards 2-acyl-3-amino-indole derivatives," *Tetrahedron Letters* (2000), 41(43), 8251-8254.

Norman, P., "Selective PI3Kδ inhibitors , a review of the patent literature", Expert Opinion on Therapeutic Patents, Informa Healthcare, 21(11):1773-1790, 2011.

Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.

Okkenhaug, et al., "Impaired B and T Cell Antigen Receptor Signaling in p110δ PI 3-Kinase Mutant Mice," Science, 2002, 297(5583):1031-4).

Park et al., Analytical Biochemistry 1999, 269, 94-104.

Park et al., "Phosphoinositide 3-kinase δ inhibitor as a novel therapeutic agent in asthma," Respirology, 13:764-771, 2008.

Phillips, et al., "The reaction of arils with 8-quinolinol," *Journal of Organic Chemistry* (1954), 19, 907-9 CODEN: JOCEAH; ISSN: 0022-3263.

Pinedo and Slamon, "Translational Research: The Role of VEGF in Tumor Angiogenesis," The Oncologist, 5(1):1-2, 2000.

Platts, et al., "A concise synthesis of HIV integrase inhibitors bearing the dipyridone acid motif," *Tetrahedron Letters* (2011), 52(4), 512-514.

(56) References Cited

OTHER PUBLICATIONS

Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).

Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.

Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.

Ramos-Casals et al., "Rituximab in systemic lupus erythematosus; A systematic review of off-label use in 188 cases," Lupus, 18:767-776, 2009.

Randis, et al., "Role of PI3Kδ and PI3Kγ in inflammatory arthritis and tissue localization of neutrophils," Eur. J. Immunol., 2008, 38(5):1215-24.

Reich, et al., "Preparation of a,b-unsaturated carbonyl compounds and nitriles by selenoxide elimination ," *Organic Reactions* (Hoboken, NJ, United States) (1993), 44, No pp. given.

Remington's Pharmaceutical Sciences, 17th ed., Mack Publishing Company, Easton, Pa., 1985, p. 1418.

Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.

Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.

Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels and Ericson, "Oncogenic PI3K and its role in cancer," Curr Opin. Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6), 445-462.
Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Selig et al., "The application of Stille cross-coupling reactions with multiple nitrogen containing heterocycles," Tetrahedron, Sep. 2011, 67(47): 9204-9213.
Segarra et al., "Successful treatment of membranous glomerulonephritis with rituximab in calcineurin inhibitor-dependent patients," Clin J Am Soc Nephroi., 2009, 4(6):1083-8.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Silverman, R. B., "The organic Chemistry of Drugs Design and Drug Action." Elselvier. Northwestern University. Second Edition. Evanstons Illinois. 2004. p. 29 and table 2.2 *Too Voluminous to Provide.
Singh et al., "Application of Nazarov cyclization to access [6-5-6] and [6-5-5]-tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stave et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," *Acta Oystallographica*, Section E: Structure Reports Online (2007), E63(2), o728-o730 CODEN: ACSEBH; ISSN: 1600-5368 URL: http://journals.iucr.org/e/issues/2007/02/00/lh2285/lh2285.pdf.
Umar, A., "Future directions in cancer prevention," Nature Reviews Cancer, 12.12 (2012): 835-848.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," *J Immunol*., 2009, 183:6472-3480.
Wallin, J.J., "GDC-0980 is a novel class I PI3K/mTOR kinase inhibitor with robust activity in cancer models driven by the PI3K pathway," Molecular cancer therapeutics 10.12 (2011): 2426-2436.
Walsh and Jayne, "Rituximab in the treatment of anti-neutrophil cytoplasm antibody associated vasculitis and systemic lupus eiythematosis: past, present and future," Kidney International, 2007, 72: 676-682.
WebMD. Arthritis Health Center: What is Inflammation? Jul. 6, 2012, www.webmd.com/arthritis/about-inflammation?page=2, 4 pages.
WebMD. Bladder Cancer Health Center: Bladder Cancer-Prevention, Apr. 30, 2013, www.webmd.com/cancer/bladder-cancer/bladder-cancer-prevention, 1 page.
WebMD. Lung Disease & Respiratory Health Center: ARDS, May 21, 2014, www.webmd.com/lung/ards-acute-respiratory-distress-syndrome?page=2, 4 pages.

(56) References Cited

OTHER PUBLICATIONS

WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skin-problems-and-treatments/psoriasis/psoriasis-prevention, 1 page.
Xu et al., "Activation of the PI3K/AKT/mTOR pathway in diffuse large B cell lymphoma: clinical significance and inhibitory effect of rituxinriab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Yuan, T.L., "PI3K pathway alterations in cancer: variations on a theme," Oncogene, 2008, 27.41: 5497-551.
Zhang et al., "Advances in preclinical small molecules for the treatment of NSCLC", Expert Opinion on Therapeutic Patents, 19(6):731-751, 2009.
Zhao and Vogt, "Class I PI3K in oncogenic cellular transformation," Oncogene, 2008, 27:5486-5496.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, issued Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STNcheck Search Report, conducted Aug. 30, 2011, 61 pages.
Office Action in CO Application No. 11-179.464, received on Mar. 14, 2014, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages (with English Translation).
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2016/031603, dated Jun. 22, 2016, 11 pages.
International Search Report and Written Opinion in International Application No. PCT/US2015/035046, dated Aug. 27, 2015, 9 pages.
International Search Report and Written Opinion in International Application No. PCT/US2016/019741, dated Aug. 2, 2016, 16 pages.
International Preliminary Report on Patentability in International Application No. PCT/US2015/035046, dated Dec. 22, 2016, 7 pages.

* cited by examiner

PROCESS FOR THE SYNTHESIS OF A PHOSPHOINOSITIDE 3-KINASE INHIBITOR

TECHNICAL FIELD

The present application relates to processes and intermediates for making (S)-7-(1-((9H-purin-6-yl)amino)ethyl)-6-(3-fluorophenyl)-3-methyl-5H-thiazolo[3,2-a]pyrimidin-5-one, and salts thereof, which modulates the activity of phosphoinositide 3-kinases (PI3Ks) and is useful in the treatment of diseases related to the activity of PI3Ks including, for example, inflammatory disorders, immune-based disorders, cancer, and other diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573): 1655-7). The compound (S)-7-(1-((9H-purin-6-yl)amino)ethyl)-6-(3-fluorophenyl)-3-methyl-5H-thiazolo[3,2-a]pyrimidin-5-one is an inhibitor of PI3Ks, including PI3Kδ, and is previously described in U.S. Pat. No. 8,940,752, which is incorporated by reference herein in its entirety.

PI3K isoforms are believed to be involved in cancer. For example, the gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Thus, inhibitors of PI3Ks, such as (S)-7-(1-((9H-purin-6-yl)amino)ethyl)-6-(3-fluorophenyl)-3-methyl-5H-thiazolo[3,2-a]pyrimidin-5-one, are potentially useful as cancer therapeutics. Accordingly, efficient and scalable syntheses are needed for producing this drug compound. The processes and intermediates provided herein are directed to this need.

SUMMARY

The present application provides, inter alia, intermediates and processes for preparing a compound of Formula (I):

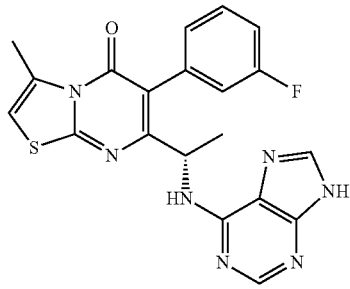

(I)

and salts thereof.

The compound of Formula (I) is an inhibitor of PI3K, including PI3Kδ, and is useful in the treatment of cancer and other diseases. The details of one or more embodiments of the invention are set forth in the accompanying drawings and the description below. Other features, objects, and advantages of the invention will be apparent from the description and drawings, and from the claims.

DETAILED DESCRIPTION

The present invention provides, inter alia, processes for preparing a compound of Formula (I):

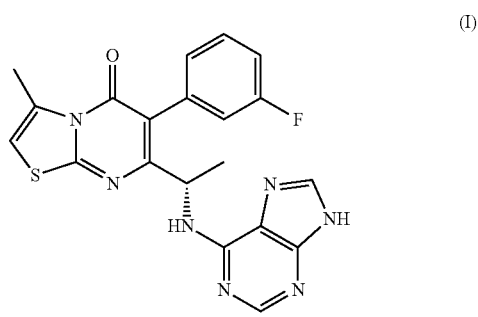 [SMILES: Cc1csc2nc([C@H](C)Nc3ncnc4[nH]cnc34)c(-c3cccc(F)c3)c(=O)n12]

(I)

or salts thereof.

In some embodiments, the process comprises reacting a compound of Formula (II):

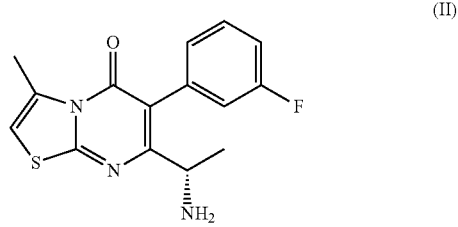 [SMILES: Cc1csc2nc([C@H](C)N)c(-c3cccc(F)c3)c(=O)n12]

(II)

with a compound of Formula (III):

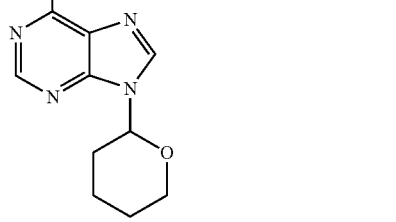

(III)

in the presence of a B1, wherein B1 is a base, to afford a compound of Formula (IV):

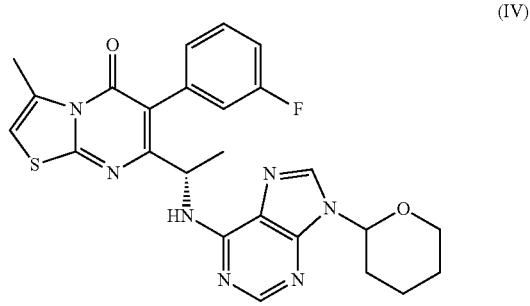

(IV)

wherein $X^1$ is halo.

In some embodiments, $X^1$ is chloro.

In some embodiments, B1 is an alkali metal bicarbonate base such as sodium bicarbonate. In some embodiments, the reacting is performed in a solvent comprising an alcohol such as isopropanol. In further embodiments, said reacting is performed at a temperature from about 80° C. to about 85° C. In yet further embodiments, about 1.1 to about 1.5 equivalents of the compound of Formula (III) is used based on 1 equivalent of the compound of Formula (II).

In some embodiments, the process further comprises deprotecting the compound of Formula (IV) in the presence of A1, wherein A1 is an acid, to afford a deprotected product which is a compound of Formula (I):

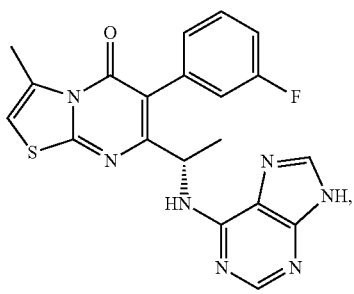

(I)

or a salt thereof.

In some embodiments, the deprotected product is a salt having Formula (Ia):

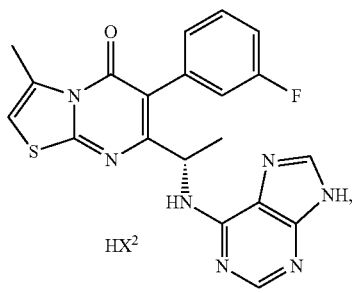

(Ia)

wherein $X^2$ is halide.

In some embodiments, $X^2$ is chloride. In some embodiments, A1 is an aqueous strong acid such as aqueous hydrochloric acid. In further embodiments, the deprotecting step is performed in a solvent comprising an alcohol such as isopropanol. In yet further embodiments, the deprotecting step is performed at a temperature from about 25° C. to about 35° C. In some embodiments, about 2.5 to about 3.5 equivalents of A1 is used based on 1 equivalent of the compound of Formula (II).

In some embodiments, the reacting and deprotecting steps are conducted in the same pot without isolation of the compound of Formula (IV).

In some embodiments, the process further comprises treating the salt of Formula (Ia) with B2, wherein B2 is a base, to form a compound of Formula (I):

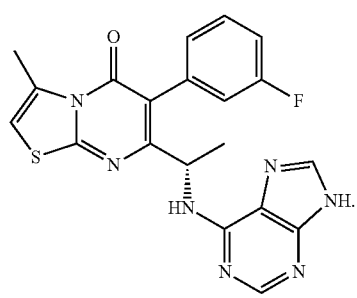

(I)

In some embodiments, B2 is an alkali metal carbonate base such as sodium carbonate. In some embodiments, the treating is performed in a solvent comprising water and a halogenated solvent such as dichloromethane. In further embodiments, about 1.5 to about 2.5 equivalents of B2 is used based on 1 equivalent of the salt of Formula (Ia). In yet further embodiments, the reacting is performed at about room temperature.

In some embodiments, the steps of reacting, deprotecting, and treating as described above result in a compound of Formula (I) in a yield of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9%.

In some embodiments, the steps of reacting, deprotecting, and treating as described above result in a compound of Formula (I) in at least about 90% yield.

In some embodiments, the steps of reacting, deprotecting, and treating as described above result in a compound of Formula (I) in greater than about 89% yield, greater than about 90% yield, greater than about 91% yield, greater than about 92% yield, greater than about 93% yield, greater than about 94% yield, greater than about 95% yield, greater than about 96% yield, greater than about 97% yield, greater than about 98% yield, or greater than about 99% yield.

In some embodiments, said compound of Formula (II) is prepared by:

(va) reacting a compound of Formula (V)

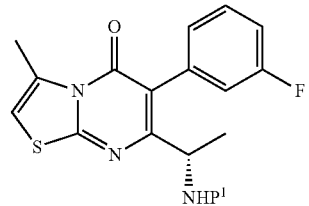

(V)

wherein $P^1$ is an amine protecting group, with A2, wherein A2 is an acid, followed by:

(vb) treating the product of the preceding step (va) with B3, wherein B3 is a base.

In some embodiments, the amine protecting group is tert-butoxycarbonyl. In some embodiments, A2 is a strong acid such as hydrochloric acid. In some embodiments, the reacting of a compound of Formula (V) is performed in the presence of a solvent such as a solvent that comprises 1,4-dioxane and water. In further embodiments, about 7 to about 9 equivalents of acid A2 is used based on 1 equivalent of the compound of Formula (V). In yet further embodiments, the reacting of a compound of Formula (V) is performed at a temperature from about 20° C. to about 30° C. In some embodiments, B3 is an alkali metal carbonate base such as sodium carbonate.

In some embodiments, the treating step (where the product of the reaction of the compound of Formula (V) is reacted with an amine protecting group is treated with B3) is performed in a solvent comprising 1,4-dioxane, water, and a halogenated solvent. In some embodiments, said halogenated solvent is dichloromethane. In further embodiments, the treating step (where the product of the reaction of the compound of Formula (V) is reacted with an amine protecting group is treated with B3) is performed at a temperature below 20° C. In yet further embodiments, about 6 to about 7 equivalents of B3 is used based on 1 equivalent of the compound of Formula (V).

In some embodiments, the compound of Formula (V) is prepared by a process comprising:

(iiia) reacting complex of Formula (VI):

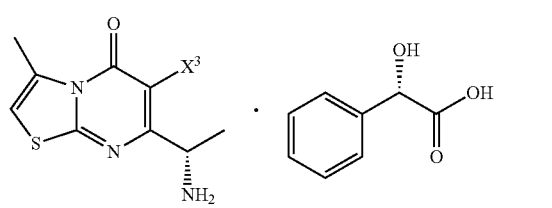

wherein X³ is halo, with an amine protecting agent in the presence of B4, wherein B4 is a base, followed by:

(iiib) reacting the product of the preceding step (iiia) with (3-fluorophenyl)boronic acid in the presence of a transition metal catalyst.

In some embodiments, the amine protecting agent is di-tert-butyl dicarbonate. In some embodiments, X³ is bromo. In some embodiments, B4 is an alkali metal carbonate base such as sodium carbonate. In further embodiments, about 1 to about 1.5 equivalents of the amine protecting agent is used based on 1 equivalent of the compound of Formula (VI). In yet further embodiments, about 3 to about 4 equivalents of B4 is used based on 1 equivalent of the compound of Formula (VI).

In some embodiments, step (iiia) is performed in the presence of solvent such as a solvent comprising 1,4-dioxane and water. In further embodiments, step (iiia) is performed at about room temperature.

In some embodiments, the transition metal catalyst is a palladium catalyst which can be selected from dichloro(bis{di-tert-butyl[4-(dimethylamino)phenyl]-phosphoranyl}) palladium (Pd-132), Pd(PPh₃)₄, Pd(dppf)₂Cl₂, and tetrakis(tri(o-tolyl)phosphine)palladium(0). In some embodiments, the palladium catalyst is dichloro(bis{di-tert-butyl[4-(dimethylamino)phenyl]-phosphoranyl})palladium (Pd-132).

In some embodiments, about 1.1 to about 1.5 equivalents of (3-fluorophenyl)boronic acid is used based on 1 equivalent of the compound of Formula (VI). In further embodiments, about 0.002 to about 0.003 equivalents of the transition metal catalyst are used based on 1 equivalent of the compound of Formula (VI). In some embodiments, step (iiib) is performed in the presence of a solvent such as a solvent comprising 1,4-dioxane and water. In further embodiments, step (iiib) is performed at an elevated temperature (e.g., higher than room temperature) such as at about reflux temperature.

In some embodiments, the compound of Formula (VI) is prepared by reacting a compound of Formula (VII):

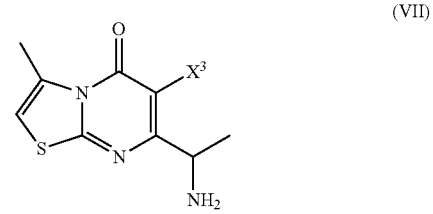

with (S)-(+)-mandelic acid.

In some embodiments, X³ is bromo.

In some embodiments, the reacting of the compound of Formula (VII) is carried out in the presence of a solvent such as a halogenated solvent like dichlormethane. In some embodiments, the compound of Formula (VII) is dissolved in a solvent prior to reacting. In some embodiments, the reacting of the compound of Formula (VII) is performed at about reflux temperature.

In some embodiments, the reaction mixture resulting from the reacting of the compound of Formula (VII) is cooled to about room temperature to afford a first precipitate. The first precipitate can be collected by filtration and combined with a further solvent. The further solvent can comprise an alcohol such as isopropanol. In some embodiments, the first precipitate which is combined with the further solvent is heated to about reflux. The refluxed mixture can be cooled to about room temperature to afford a second precipitate, which can be collected by filtration.

In some embodiments, about 0.25 to about 0.75 equivalents of (S)-(+)-mandelic acid is used based on 1 equivalent of the compound of Formula (VII).

In some embodiments, a preparation of Formula (VI) for use as a reagent or obtained as a product has a chiral purity of greater than about 99.5%.

In some embodiments, the compound of Formula (III) is prepared by reacting a compound of Formula (VIII):

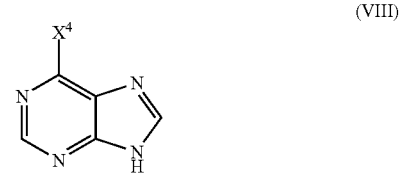

wherein X⁴ is halo, with 3,4-dihydro-2H-pyran in the presence of a A3, wherein A3 is an acid. In some embodiments, X⁴ is chloro. In some embodiments, A3 is a strong organic acid, such asp-toluenesulfonic acid.

In some embodiments, about 1.2 to about 1.7 equivalents of 3,4-dihydro-2H-pyran is used based on 1 equivalent of the compound of Formula (VIII). In some embodiments, about 1.0 to about 7 equivalents of 3,4-dihydro-2H-pyran is used based on equivalent of the compound of Formula (VIII). In some embodiments, about 1.0 to about 5 equivalents of 3,4-dihydro-2H-pyran is used based on 1 equivalent of the compound of Formula (VIII). In some embodiments, about 1.0 to about 3 equivalents of 3,4-dihydro-2H-pyran is used based on 1 equivalent of the compound of Formula (VIII).

In some embodiments, about 1.0 to about 2 equivalents of 3,4-dihydro-2H-pyran is used based on 1 equivalent of the compound of Formula (VIII). In some embodiments, about 1.2 to about 7 equivalents of 3,4-dihydro-2H-pyran is used based on 1 equivalent of the compound of Formula (VIII). In some embodiments, about 1.2 to about 5 equivalents of 3,4-dihydro-2H-pyran is used based on 1 equivalent of the compound of Formula (VIII).

In some embodiments, about 1.2 to about 3 equivalents of 3,4-dihydro-2H-pyran is used based on 1 equivalent of the compound of Formula (VIII). In some embodiments, about 1.2 to about 2 equivalents of 3,4-dihydro-2H-pyran is used based on 1 equivalent of the compound of Formula (VIII).

In some embodiments, the reacting of a compound of Formula (VIII) is performed in a solvent comprising a halogenated solvent such as dichloromethane.

In some embodiments, the reacting of a compound of Formula (VIII) is performed at about room temperature.

In some embodiments, the compound of Formula (VII) is prepared by i) reacting a compound of Formula (IX):

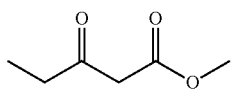
(IX)

with a halogen to form a compound of Formula (X):

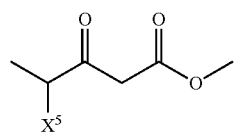
(X)

wherein $X^5$ is halo;

ii) reacting the compound of Formula (X) with 4-methylthiazol-2-amine in the presence of A4, wherein A4 is a strong acid, to form a compound of Formula (XI):

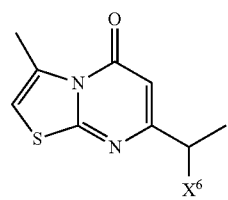
(XI)

iii) reacting the compound of Formula (XI) with an N-halosuccinimide to form a compound of Formula (XII):

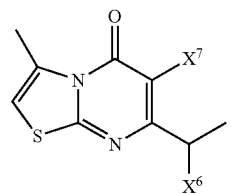
(XII)

wherein $X^7$ is halo;

iv) reacting the compound of Formula (XII) with an alkali metal azide to form a compound of Formula (XIII):

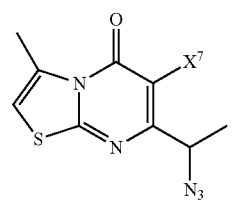
(XIII)

and v) reacting the compound of Formula (XIII) with TMS-$X^8$ in the presence of an alkali metal halide to form a compound of Formula (VII):

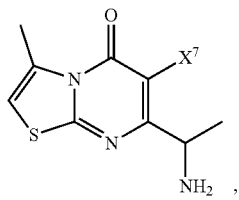
(VII)

wherein $X^8$ is halo.

In some embodiments, the halogen is bromine.
In some embodiments, $X^5$ is bromo.
In some embodiments, A4 is polyphosphoric acid.
In some embodiments, the N-halosuccinimide is N-bromosuccinimide.
In some embodiments, $X^6$ is bromo.
In some embodiments, said alkali metal azide is sodium azide.
In some embodiments, $X^7$ is bromo.
In some embodiments, the alkali metal halide is sodium iodide.
In some embodiments, $X^8$ is chloro.
In some embodiments, step i) comprises reacting a compound of Formula (IX):

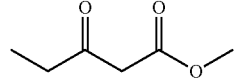
(IX)

with bromine to form a compound of Formula (Xa):

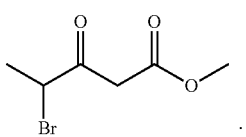
(Xa)

In some embodiments, step ii) comprises reacting the compound of Formula (Xa) with 4-methylthiazol-2-amine in the presence of polyphosphoric acid to form a compound of Formula (XIa):

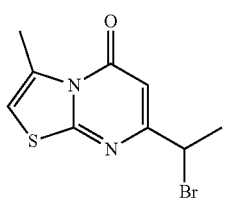
(XIa)

In some embodiments, step iii) comprises reacting the compound of Formula (XIa) with N-bromosuccinimide to form a compound of Formula (XIIa):

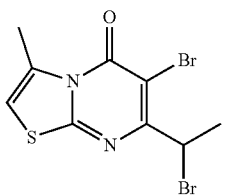
(XIIa)

In some embodiments, step iv) comprises reacting the compound of Formula (XIIa) with sodium azide to form a compound of Formula (XIIIa):

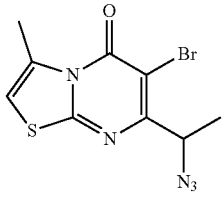
(XIIIa)

In some embodiments, step v) comprises reacting the compound of Formula (XIIIa) with TMS-Cl in the presence of sodium iodide to form a compound of Formula (VIIa):

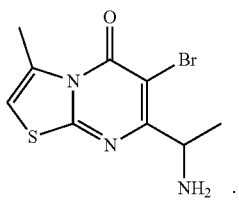
(VIIa)

The present application also provides a process of preparing a compound of Formula (I), comprising:

i) reacting a compound of Formula (IX):

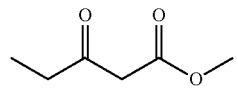
(IX)

with bromine to form a compound of Formula (Xa):

(Xa)

ii) reacting the compound of Formula (Xa) with 4-methylthiazol-2-amine in the presence of polyphosphoric acid to form a compound of Formula (XIa):

(XIa)

iii) reacting the compound of Formula (XIa) with N-bromosuccinimide to form a compound of Formula (XIIa):

(XIIa)

iv) reacting the compound of Formula (XIIa) with sodium azide to form a compound of Formula (XIIIa):

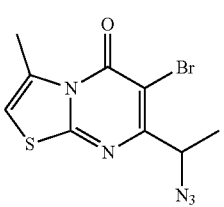
(XIIIa)

v) reacting the compound of Formula (XIIIa) with TMS-Cl in the presence of sodium iodide to form a compound of Formula (VIIa):

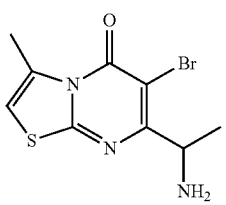
(VIIa)

vi) reacting the compound of Formula (VIIa) with (S)-(+)-mandelic acid to form a compound of Formula (VIa):

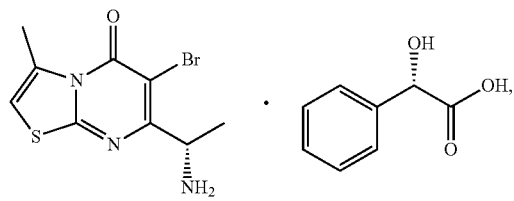
(VIa)

vii) protecting the compound of Formula (VIa) with di-tert-butyl dicarbonate in the presence of sodium carbonate;

viii) reacting the product of the previous step (step vii) with (3-fluorophenyl)boronic acid in the presence of dichloro(bis{di-tert-butyl[4-(dimethylamino)phenyl]-phosphoranyl})palladium (Pd-132) to form a compound of Formula (Va):

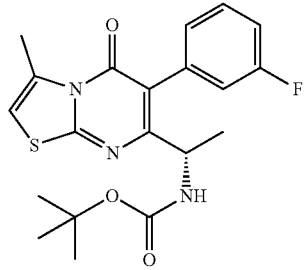
(Va)

ix) reacting the compound of Formula (Va) with hydrochloric acid;

x) reacting the product of the previous step (step ix) with sodium carbonate to form a compound of Formula (II):

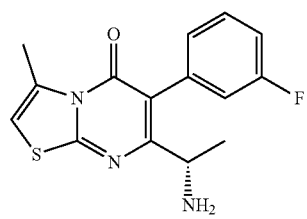
(II)

xi) reacting the compound of Formula (II) with a compound of Formula (IIIa):

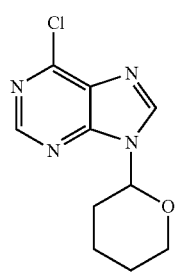
(IIIa)

in the presence of sodium carbonate to afford a compound of Formula (IV):

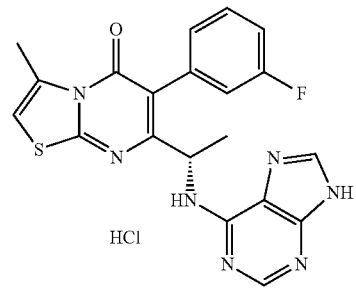
(IVa)

xii) deprotecting the compound of Formula (IVa) in the presence of hydrochloric acid to form a salt of Formula (Ib):

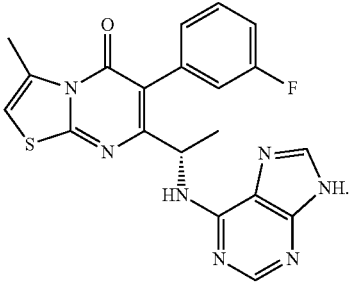
(Ib)

and xiii) reacting the salt of Formula (Ib) with sodium carbonate to form a compound of Formula (I):

(I)

In some embodiments, the overall yield of steps xi) to xiii) is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9%.

In some embodiments, the overall yield of steps xi) to xiii) is about 90%.

In some embodiments, the overall yield of steps xi) to xiii) is greater than about 89% yield, greater than about 90% yield, greater than about 91% yield, greater than about 92% yield, greater than about 93% yield, greater than about 94% yield, greater than about 95% yield, greater than about 96% yield, greater than about 97% yield, greater than about 98% yield, or greater than about 99% yield.

The present invention also provides a process of preparing a compound of Formula (I), comprising:

i) reacting a compound of Formula (VIIa)

(VIIa)

with (S)-(+)-mandelic acid to form a compound of Formula (VIa)

(VIa)

ii) protecting the compound of Formula (VIa) with di-tert-butyl dicarbonate in the presence of sodium carbonate;

iii) reacting the product of step ii) with (3-fluorophenyl) boronic acid in the presence of dichloro(bis {di-tert-butyl [4-(dimethylamino)phenyl]-phosphoranyl})palladium (Pd-132) to form a compound of Formula (Va):

(Va)

iv) reacting the compound of Formula (Va) with hydrochloric acid;

v) reacting the product of step iv) with sodium carbonate to form a compound of Formula (II):

(II)

vi) reacting the compound of Formula (II) with a compound of Formula (IIIa):

(IIIa)

in the presence of sodium carbonate to afford a compound of Formula (IV):

(IV)

vii) deprotecting the compound of Formula (IV) with hydrochloric acid to form a salt of Formula (Ib):

(Ib)

and viii) reacting the salt of Formula (Ib) with sodium carbonate to form a compound of Formula (I):

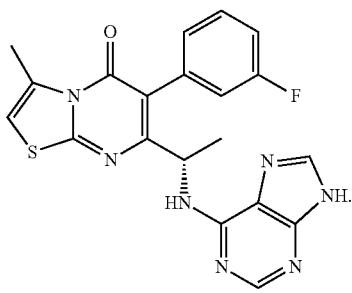

(I)

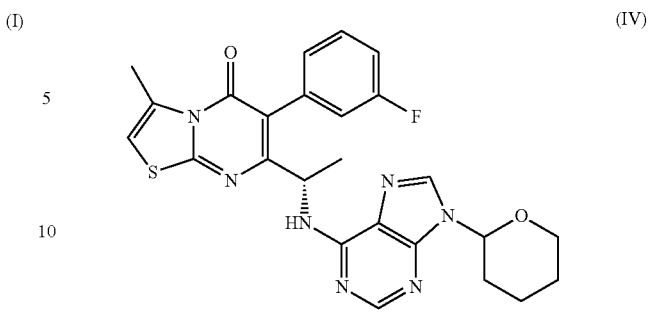

(IV)

In some embodiments, the overall yield of steps vi) to viii) is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9%.

In some embodiments, the overall yield of steps vi) to viii) is about 90%.

In some embodiments, the overall yield of steps xi) to xiii) is greater than about 89% yield, greater than about 90% yield, greater than about 91% yield, greater than about 92% yield, greater than about 93% yield, greater than about 94% yield, greater than about 95% yield, greater than about 96% yield, greater than about 97% yield, greater than about 98% yield, or greater than about 99% yield.

The present application also provides a compound of Formula (III):

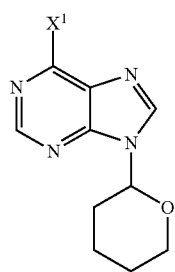

(III)

or a salt thereof, wherein X¹ is halo.

In some embodiments, the compound of Formula (III) is a compound of Formula (IIIa):

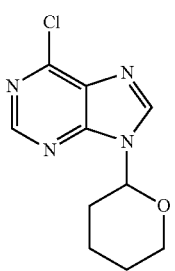

(IIIa)

or a salt thereof.

The present application also provides a compound of Formula (IV):

or a salt thereof.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

As used herein, the expression "alkali metal azide," employed alone or in combination with other terms, refers to an azide having formula $MN_3$, wherein M refers to an alkali metal (e.g. lithium, sodium, or potassium). Example alkali metal azides include, but are not limited to, lithium azide, sodium azide, and potassium azide.

As used herein, the expression "alkali metal bicarbonate base," employed alone or in combination with other terms, refers to a base having formula $M(HCO_3)$, wherein M refers to an alkali metal (e.g. lithium, sodium, or potassium). Example alkali metal bicarbonate bases include, but are not limited to, lithium bicarbonate, sodium bicarbonate, and potassium bicarbonate.

As used herein, the expression "alkali metal carbonate base," employed alone or in combination with other terms, refers to a base having formula $M_2CO_3$, wherein M refers to an alkali metal (e.g. lithium, sodium, or potassium). Example alkali metal carbonate bases include, but are not limited to lithium carbonate, sodium carbonate, and potassium carbonate.

As used herein, "halo," employed alone or in combination with other terms, includes fluoro, chloro, bromo, and iodo.

As used herein, "halogen" refers to elemental halogens, like $Cl_2$ or $Br_2$.

As used herein, "halide," employed alone or in combination with other terms, includes fluoride, chloride, bromide, and iodide.

As used herein, the term "transition metal catalyst" refers to a metal catalyst (e.g., palladium or nickel catalyst) suitable to catalyze a carbon-carbon coupling reaction. Example transition metal catalysts include, but are not limited to, $PdCl_2(PPh_3)_2$, $Pd(PPh_3)_4$, dichloro(bis{di-tert-butyl[4-(dimethylamino)phenyl]-phosphoranyl})palladium (Pd-132), $NiCl_2$(dppf), and $NiCl_2$(dppp), where (dppf) refers to 1,1'-bis(diphenylphosphino)ferrocene and (dppp) refers to 1,3-bis(diphenylphosphino)propane.

Example palladium catalysts include but are not limited to $PdCl_2(PPh_3)_2$, $Pd(PPh_3)_4$, dichloro(bis{di-tert-butyl[4-(dimethylamino)phenyl]-phosphoranyl})palladium (Pd-132), palladium on carbon, $PdCl_2$, $Pd(OAc)_2$, $PdCl_2(MeCN)_2$, and tris(dibenzylideneacetone)dipalladium(0).

As used herein, the terms "reacting," "treating," and "combining," are used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out in air or under an inert atmosphere. Typically, reactions containing reagents or products that are substantially reactive with air can be carried out using air-sensitive synthetic techniques that are well known to the skilled artisan.

As used herein, the expression, "room temperature," is understood in the art, and refers generally to a temperature (e.g. a reaction temperature) that is about the temperature of the room in which the reaction is carried out, for example, a temperature from about 20° C. to about 30° C.

Preparation of the compounds described herein can involve the protection and deprotection of various chemical groups (e.g., protection and deprotection of amine groups). The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety. Adjustments to the protecting groups and formation and cleavage methods described herein may be adjusted as necessary in light of the various substituents.

As used herein, the term "deprotecting" refers to conditions suitable to cleave a protecting group, such as an amine protecting group. In some embodiments, deprotecting may include cleavage of a protecting group in the presence of a strong acid, in the presence of a strong base, in the presence of a reducing agent, or in the presence of an oxidizing agent. Deprotection of an amine protecting group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the treating comprises reacting the amine-protected compound under acidic conditions (e.g., treating with hydrochloric acid or trifluoroacetic acid). In some embodiments, the temperature is about room temperature, at a temperature from about 15° C. to about 40° C., or at a temperature from about 15° C. to about 30° C.

As used herein, the term "protecting" refers to reaction of a compound with a reagent that results in the addition of a protecting group to the compound, such as an amine protecting group.

Appropriate $P^1$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety.

Example amine protecting groups include, but are not limited to, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP), tri($C_{1-4}$ alkyl)silyl (e.g., tri(isopropyl)silyl), 1,1-diethoxymethyl, or N-pivaloyloxymethyl (POM).

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The following abbreviations may be used herein: aq. (aqueous); Boc (t-butoxycarbonyl); Br$_2$ (bromine); 1-BuOH (1-butanol); calc. (calculated); d (doublet); dd (doublet of doublets); DCM (dichloromethane); DIPEA (N,N-diisopropylethylamine); DMF (N,N-dimethylformamide); e.e. (enantiomeric excess); eq. (equivalents); Et (ethyl); Et$_2$O (diethyl ether); EtOAc (ethyl acetate); EtOH (ethanol); g (gram(s)); h (hour(s)); HCl (hydrochloric acid/hydrogen choride); HPLC (high performance liquid chromatography); Hz (hertz); IPA (isopropyl alcohol); J (coupling constant); LCMS (liquid chromatography-mass spectrometry); m (multiplet); M (molar); Me (methyl); MeCN (acetonitrile); MeOH (methanol); mg (milligram(s)); min. (minutes(s)); mL (milliliter(s)); mmol (millimole(s)); MS (Mass spectrometry); MTBE (methyl tert-butyl ether); N (normal); NBS (N-bromosuccinimide); Na$_2$CO$_3$ (sodium carbonate); NaHCO$_3$ (sodium bicarbonate); NaHSO$_3$ (sodium bisulfite); NaI (sodium iodide); NaN$_3$ (sodium azide); NaOH (sodium hydroxide); Na$_2$SO$_3$ (sodium sulfite); Na$_2$SO$_4$ (sodium sulfate); Na$_2$S$_2$O$_3$ (sodium thiosulfate); nM (nanomolar); NMR (nuclear magnetic resonance spectroscopy); Pd (palladium); Pd-132 (dichloro(bis{di-tert-butyl[4-(dimethylamino)phenyl]-phosphoranyl})palladium); PdCl$_2$(MeCN)$_2$ (bis(acetonitrile)dichloropalladium(II)); Pd(OAc)$_2$ (palladium acetate); pM (picomolar); PPA (polyphosphoric acid); PTSA (p-toluenesulfonic acid); RP-HPLC (reverse phase high performance liquid chromatography); sat. (saturated); t (triplet or tertiary); t-Bu (tert-butyl); TFA (trifluoroacetic acid); THF (tetrahydrofuran); TLC (thin layer chromatography); μg (microgram(s)); μL (microliter(s)); μM (micromolar); wt % (weight percent).

Methods

The compound Formula (I) can inhibit activity of one or more of various kinases including, for example, phosphoinositide 3-kinases (PI3Ks), including PI3Kδ.

Given that cancer cell growth and survival is impacted by multiple signaling pathways, the compound of Formula (I) is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reducing the likelihood of drug-resistance arising in a cell, and reducing the toxicity of treatments for disease.

Kinases to which the compound of Formula (I) may bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

The compound of Formula (I) is useful in treating a kinase (such as PI3K)-associated disease or disorder in an individual (e.g., patient) by administering to the individual in need of such treatment a therapeutically effective amount or dose of one or more compounds of the present application or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjoegren's syndrome, and the like.

Further examples of PI3K-associated diseases include idiopathic thrombocytopenic purpura (ITP), autoimmune hemolytic anemia (AIHA), vasculitis, systemic lupus erythematosus, lupus nephritis, pemphigus, membranous nephropathy, chronic lymphocytic leukemia (CLL), Non-Hodgkin lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the present application provides a method of treating pemphigus, membranous nephropathy, Hodgkin's lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), or monoclonal gammopathy of undetermined significance (MGUS).

In some embodiments, the present application provides a method of treating osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome.

In some embodiments, the disease is idiopathic thrombocytopenic purpura (ITP), autoimmune hemolytic anemia (AIHA), vasculitis, pemphigus, or membranous nephropathy.

In some embodiments, the idiopathic thrombocytopenic purpura (ITP) is selected from relapsed ITP and refractory ITP.

In some embodiments, the vasculitis is selected from Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schonlein purpura (HSP), hypersensitivity vasculitis, microscopic polyangiitis, Wegener's granulomatosis, and anti-neutrophil cytoplasm antibody associated (ANCA) systemic vasculitis (AASV).

In some embodiments, the compound of Formula (I) is useful in treating an immune-based disease, cancer, or lung disease in a patient. In some embodiments, the immune-based disease is systemic lupus erythematosus or lupus nephritis. In some embodiments, the cancer is breast cancer, prostate cancer, colon cancer, endometrial cancer, brain cancer, bladder cancer, skin cancer, cancer of the uterus, cancer of the ovary, lung cancer, pancreatic cancer, renal cancer, gastric cancer, or a hematological cancer. In some embodiments, the hematological cancer is acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma. In some embodiments, the non-Hodgkin lymphoma (NHL) is selected from relapsed NHL, refractory NHL, and recurrent follicular NHL. In some embodiments, the lung disease is acute lung injury (ALI) or adult respiratory distress syndrome (ARDS).

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies One or more additional pharmaceutical agents such as, for example, chemotherapeutics, anti-inflammatory agents, steroids, immunosuppressants, as well as Bcr-Abl, Flt-3, EGFR, HER2, JAK (e.g., JAK1 or JAK2), c-MET, VEGFR, PDGFR, cKit, IGF-1R, RAF, FAK, Akt mTOR, PIM, and AKT (e.g., AKT1, AKT2, or AKT3) kinase inhibitors such as, for example, those described in WO 2006/056399, or other agents such as, therapeutic antibodies can be used in combination with the compound of Formula (I) for treatment of PI3K-associated diseases, disorders or conditions. The one or more additional pharmaceutical agents can be administered to a patient simultaneously or sequentially.

In some embodiments, the additional pharmaceutical agent is a JAK1 and/or JAK2 inhibitor. In some embodiments, the present application provides a method of treating a disease described herein (e.g., a B cell malignancy, such as diffuse B-cell lymphoma) in a patient comprising administering to the patient a compound described herein, or a pharmaceutically acceptable salt thereof, and a JAK1 and/or JAK2 inhibitor. The B cell malignancies can include those described herein and in U.S. Ser. No. 61/976,815, filed Apr. 8, 2014. In some embodiments, the inhibitor of JAK1 and/or JAK2 is 3-cyclopentyl-3-[4-(7H-pyrrolo[2,3-d]pyrimidin-4-yl)-1H-pyrazol-1-yl]propanenitrile. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl] propanenitrile (ruxolitinib; also known as INCB018424). Ruxolitinib has an $IC_{50}$ of less than 10 nM at 1 mM ATP (assay D) at JAK1 and JAK2. 3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the inhibitor of JAK1 and/or JAK2 is a compound of Table A, or a pharmaceutically acceptable salt thereof. The compounds in Table A are selective JAK1 inhibitors (selective over JAK2, JAK3, and TYK2). The $IC_{50}$s obtained by the method of Assay D at 1 mM ATP are shown in Table A.

TABLE A

| # | Prep. | Name | Structure | JAK1 $IC_{50}$ (nM) | JAK2/JAK1 |
|---|---|---|---|---|---|
| 1 | Example J1 herein | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 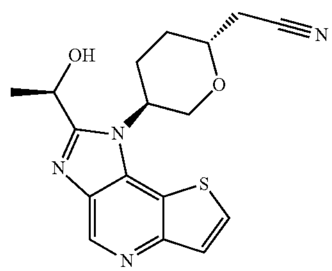 [SMILES: C[C@@H](O)c1nc2cnc3ccsc3c2n1[C@H]1CC[C@H](CC#N)OC1] | ++ | >10 |
| 2 | Example J2 herein | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 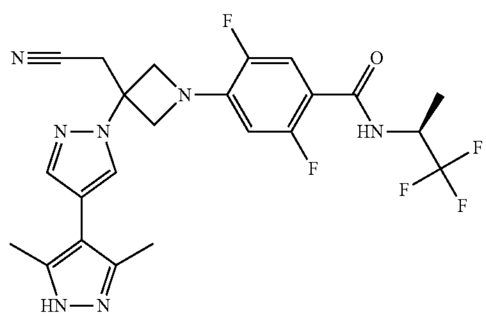 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 3 | US 2010/0298334 Ex. 2[a] | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 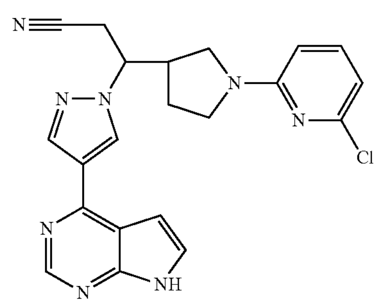 [SMILES: N#CCC(C1CCN(c2cccc(Cl)n2)C1)n1cc(-c2ncnc3[nH]ccc23)cn1] | + | >10 |
| 4 | US 2010/0298334 Ex. 13c | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 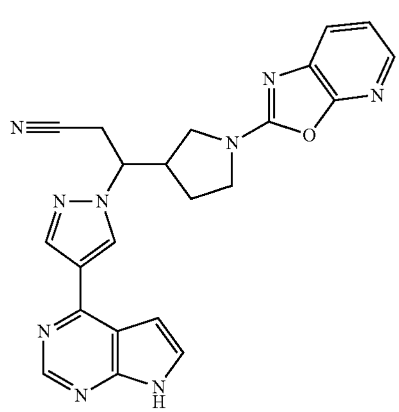 [SMILES: N#CCC(C1CCN(c2nc3cccnc3o2)C1)n1cc(-c2ncnc3[nH]ccc23)cn1] | + | >10 |

TABLE A-continued

| # | Prep. | Name | Structure | JAK1 IC$_{50}$ (nM) | JAK2/JAK1 |
|---|---|---|---|---|---|
| 5 | US 2011/0059951 Ex. 12 | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 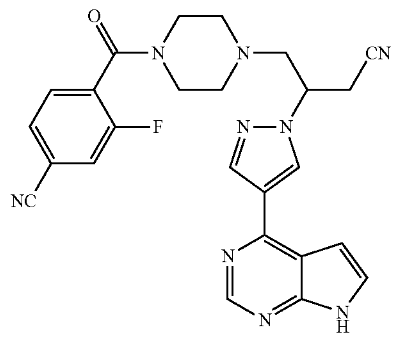 [SMILES: N#CCC(CN1CCN(C(=O)c2ccc(C#N)cc2F)CC1)n1cc(-c2ncnc3[nH]ccc23)cn1] | + | >10 |
| 6 | US 2011/0059951 Ex. 13 | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 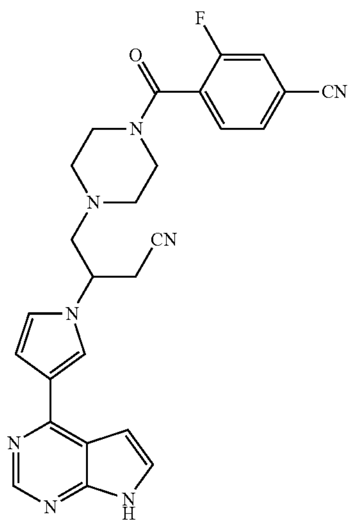 [SMILES: N#CCC(CN1CCN(C(=O)c2ccc(C#N)cc2F)CC1)n1ccc(-c2ncnc3[nH]ccc23)c1] | + | >10 |
| 7 | US 2011/0224190 Ex. 1 | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 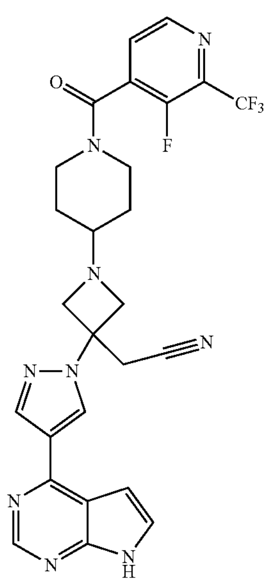 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE A-continued

| # | Prep. | Name | Structure | JAK1 IC$_{50}$ (nM) | JAK2/JAK1 |
|---|---|---|---|---|---|
| 8 | US 2011/ 0224190 Ex. 154 | 4-{3-(Cyanomethyl)- 3-[4-(7H-pyrrolo[2,3- d]pyrimidin-4-yl)-1H- pyrazol-1-yl]azetidin- 1-yl}-N-[4-fluoro-2- (trifluoromethyl)phenyl] piperidine-1- carboxamide | 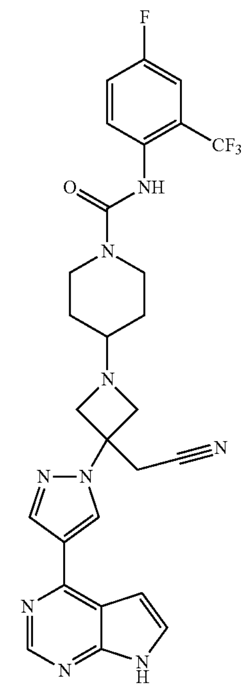 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 9 | US 2011/ 0224190 Ex. 85 | [3-[4-(7H-pyrrolo[2,3- d]pyrimidin-4-yl)-1H- pyrazol-1-yl]-1-(1- {[2- (trifluoromethyl)pyrim- idin-4- yl]carbonyl}piperidin- 4-yl)azetidin-3- yl]acetonitrile | 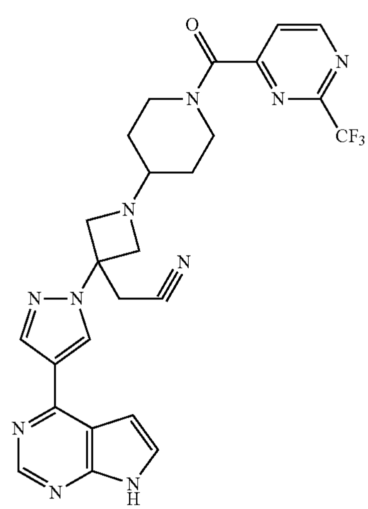 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE A-continued

| # | Prep. | Name | Structure | JAK1 IC$_{50}$ (nM) | JAK2/JAK1 |
|---|---|---|---|---|---|
| 10 | US 2012/0149681 Ex. 7b | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 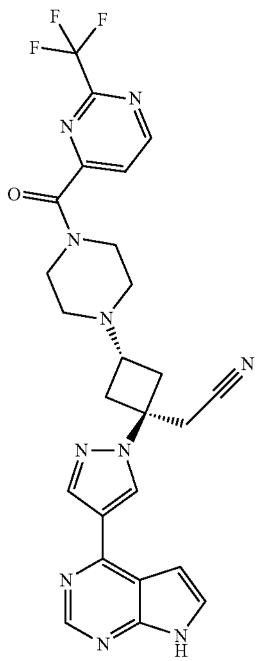 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/0149681 Ex. 157 | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 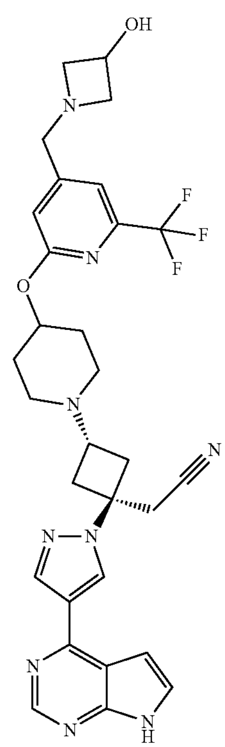 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 12 | US 2012/ 0149681 Ex. 161 | {trans-3-(4-{[4-{[(2S)-2-(hydroxymethyl) pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 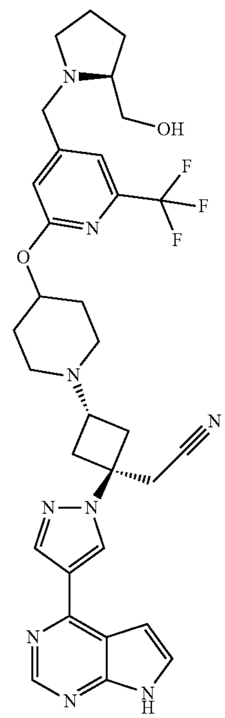 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 Ex. 162 | {trans-3-(4-{[4-{[(2R)-2-(hydroxymethyl) pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 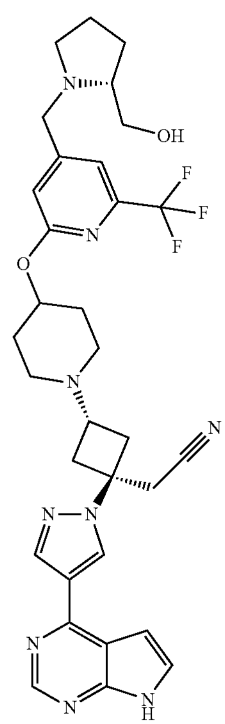 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 14 | US 2012/ 0149682 Ex. 20[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 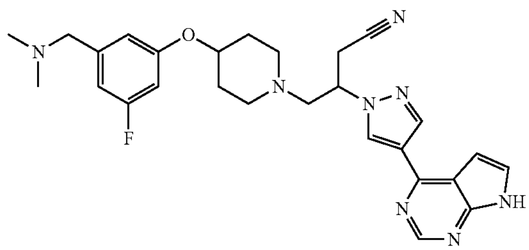 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 Ex. 18 | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 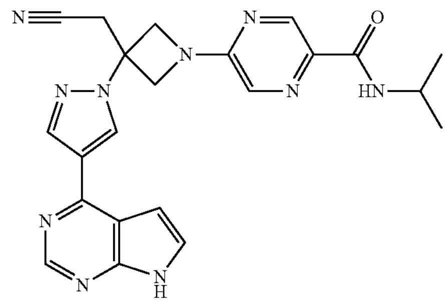 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 Ex. 28 | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 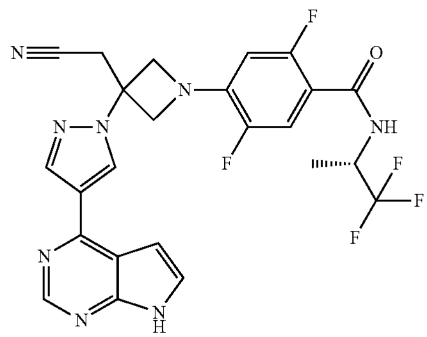 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 Ex. 34 | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 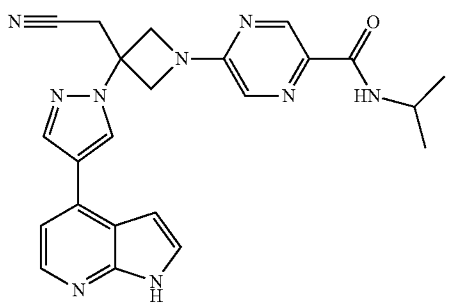 [SMILES: CC(C)NC(=O)c1cnc(N2CC(CC#N)(n3cc(-c4ccnc5[nH]ccc45)cn3)C2)cn1] | + | >10 |
| 18 | US 2013/ 0045963 Ex. 45 | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 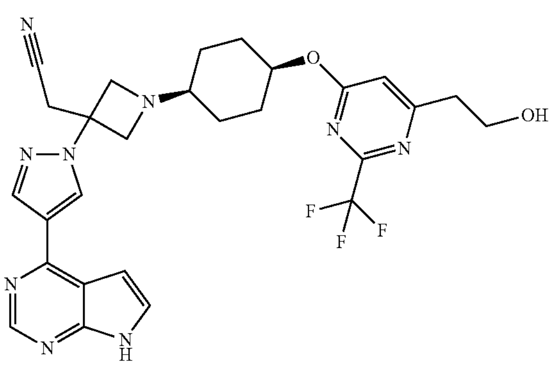 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |

TABLE A-continued

| # | Prep. | Name | Structure | JAK1 IC$_{50}$ (nM) | JAK2/JAK1 |
|---|---|---|---|---|---|
| 19 | US 2013/0045963 Ex. 65 | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl]acetonitrile | 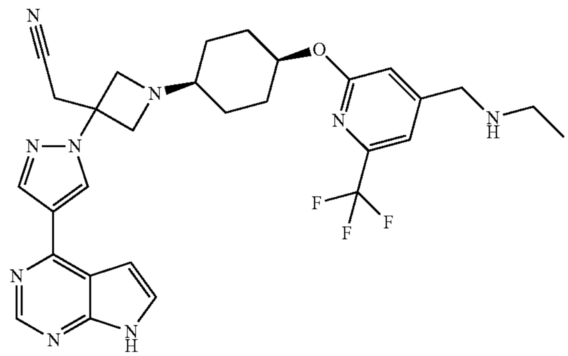 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 Ex. 69 | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 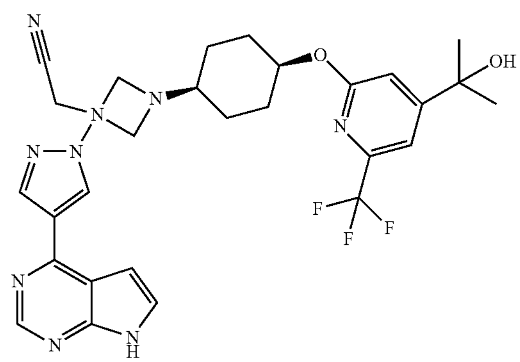 | + | >10 |
| 21 | US 2013/0045963 Ex. 95 | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 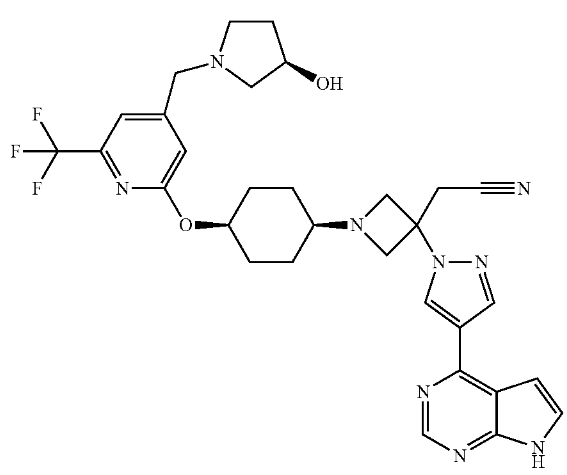 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 22 | US 2013/ 0045963 Ex. 95 | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 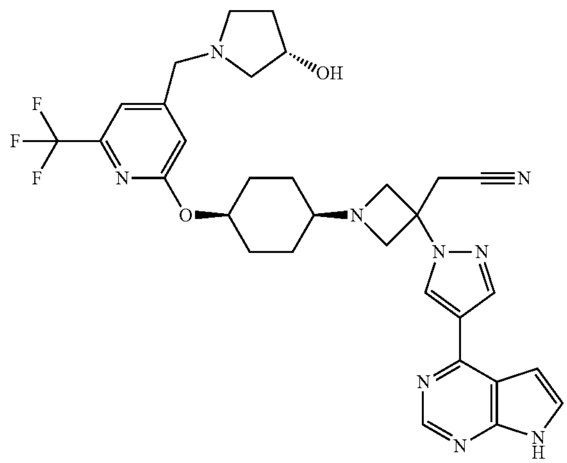 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 Ex. 1 | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 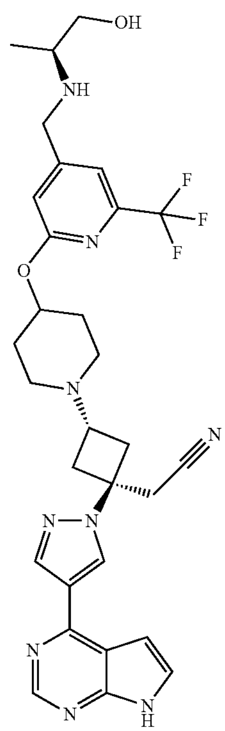 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Prep. | Name | Structure | JAK1 IC$_{50}$ (nM) | JAK2/JAK1 |
|---|---|---|---|---|---|
| 24 | US 2014/0005166 Ex. 14 | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 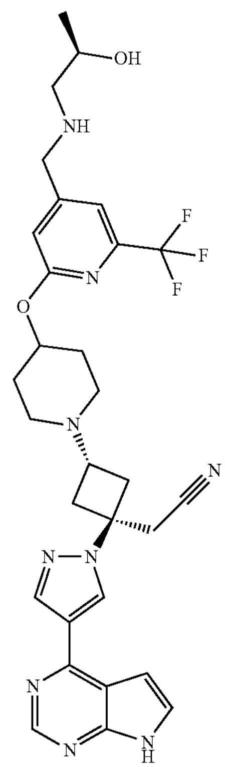 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/0005166 Ex. 15 | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 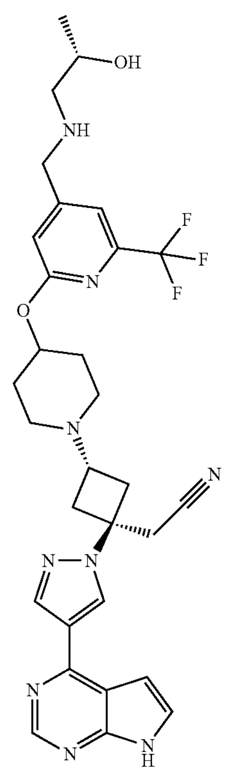 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Prep. | Name | Structure | JAK1 IC$_{50}$ (nM) | JAK2/ JAK1 |
|---|---|---|---|---|---|
| 26 | US 2014/ 0005166 Ex. 20 | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 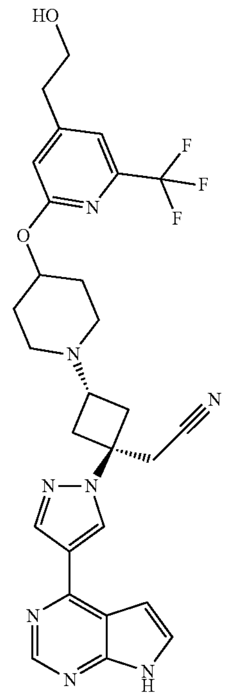 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example D for assay conditions)
++ means ≤100 nM (see Example D for assay conditions)
+++ means ≤300 nM (see Example D for assay conditions)
$^a$Data for enantiomer 1
$^b$Data for enantiomer 2

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the inhibitor of JAK1 and/or JAK2 is 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1 S)-2,2,2-trifluoro-1-methylethyl]benzamide, or a pharmaceutically acceptable salt thereof.

In some embodiments, the inhibitor of JAK1 and/or JAK2 is selected from (R)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (R)-3-(1-[1,3]oxazolo[5,4-b]pyridin-2-ylpyrrolidin-3-yl)-3-[4-(7H-pyrrolo[2, 3-d]pyrimidin-4-yl)-1H-pyrazol-1-yl]propanenitrile, (R)-4-[(4-{3-cyano-2-[4-(7H-pyrrolo[2, 3-d]pyrimidin-4-yl)-1H-pyrazol-1-yl]propyl}piperazin-1-yl)carbonyl]-3-fluorobenzonitrile, (R)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or (R)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile, (S)-3-[1-(6-chloropyridin-2-yl)pyrrolidin-3-yl]-3-[4-(7H-pyrrolo[2, 3-d]pyrimidin-4-yl)-1H-pyrazol-1-yl]propanenitrile, (S)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (S)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (S)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, (S)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile; and pharmaceutically acceptable salts of any of the aforementioned.

In some embodiments, the compounds of Table A are prepared by the synthetic procedures described in US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the inhibitor of JAK1 and/or JAK2 is selected from the compounds of US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No.

2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compound of Formula (I) and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, bendamustine (Treanda), ofatumumab, and GS-1101 (also known as CAL-101).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the compound of Formula (I) can be used in combination with one or more other kinase inhibitors including imatinib, particularly for treating patients resistant to imatinib or other kinase inhibitors.

In some embodiments, the compound of Formula (I) can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present application with an additional agent. Furthermore, resistance of multiple myeloma cells to agents such as dexamethasone may be reversible upon treatment with the PI3K inhibitor of the present application. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

Pharmaceutical Formulations and Dosage Forms

When employed as pharmaceuticals, the compound of Formula (I) can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, the compound of Formula (I) or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Milling procedures, such as wet milling, to obtain a particle size appropriate for tablet formation and for other formulation types can be carried out. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, compositions contain from about 5 to about 50 mg of the active ingredient. One having ordinary skill in the art will appreciate that this embodies compounds or compositions containing about 5 to about 10, about 10 to about 15, about to about 20, about 20 to about 25, about 25 to about 30, about 30 to about 35, about 35 to about 40, about 40 to about 45, or about 45 to about 50 mg of the active ingredient.

In some embodiments, compositions contain from about 50 to about 500 mg of the active ingredient. One having ordinary skill in the art will appreciate that this embodies compounds or compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions contain from about 500 to about 1000 mg of the active ingredient. One having ordinary skill in the art will appreciate that this embodies compounds or compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present application. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present application.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present application can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compositions can further include one or more additional pharmaceutical agents such as a chemotherapeutic, steroid, anti-inflammatory compound, or immunosuppressant, examples of which are listed herein.

Labeled Compounds and Assay Methods

Another aspect of the present application relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present application includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, one or more H atoms for any crystalline form described herein is each replaced by a deuterium atom.

The present application can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present application also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Intermediate 1. (+)-7-(1-Aminoethyl)-6-bromo-3-methyl-5H-thiazolo[3,2-a]pyrimidin-5-one (7)

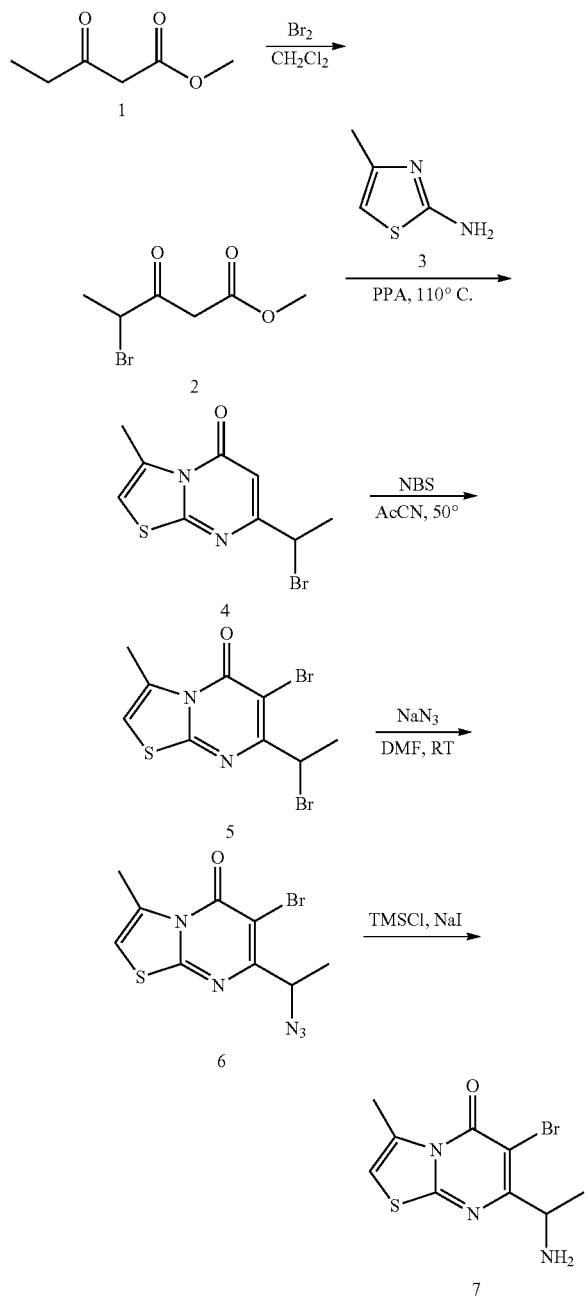

Step 1. Methyl 4-bromo-3-oxopentanoate

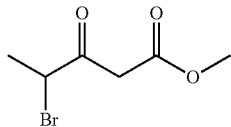

A 5 L, three-necked, round-bottomed flask was fitted with a mechanical stirrer, a pressure-equalizing addition funnel equipped with a nitrogen inlet, and a distillation assembly set for downward distillation to a 500-mL receiving flask. The outlet of the distillation assembly was attached to a 5-L trap, a NaOH (25%, 300 mL) trap, and a trap with an aqueous solution of NaOH (25%, 200 mL) containing $Na_2S_2O_3$ (30 g). The three necked flask was charged with a solution of 3-oxopentanoic acid methyl ester (500.0 g, 3842 mmol) in DCM (2000 mL) and the resulting solution was cooled with an ice-water bath. Under nitrogen, a solution of bromine (208 mL, 4030 mmol, 1.05 equiv) in DCM (200 mL) was added drop-wise via an addition funnel over about 20-30 min. The resulting reaction mixture was warmed to room temperature and stirred for 30 min. Reaction progress was monitored via $^1$H-NMR. Upon completion of the reaction, the mixture was distilled at atmospheric pressure until the solution temperature reached 55° C. to afford crude methyl 4-bromo-3-oxopentanoate (2) as a golden colored liquid, which was used directly in the next step without further purification. $^1$H NMR (400 MHz, DMSO-$d_6$) δ 4.89 (q, J=6.9 Hz, 1H), 3.85 (s, 2H), 3.63 (s, 3H), 1.64 (d, J=6.7 Hz, 3H).

Step 2. 7-(1-Bromoethyl)-3-methyl-5H-thiazolo[3,2-a]pyrimidin-5-one

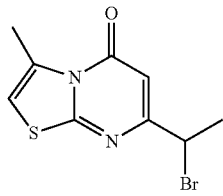

A 12-L, three-necked, round-bottomed flask was fitted with a mechanical stirrer, a J-KEM temperature controller, and a condenser equipped with a nitrogen inlet. The flask was charged with polyphosphoric acid (PPA, 2002 g, 18.36 mol, assay of phosphate as $P_2O_5$>83%) and heated to ~70° C. to give a free flowing liquid. With stirring, 4-methyl-1,3-thiazol-2-amine (3, 400.0 g, 3504 mmol) was added in small portions via a powder funnel. The resulting mixture was stirred until good mixing was achieved. Crude methyl 4-bromo-3-oxopentanoate (2, 3842 mmol, 1.1 equiv) was then added to the flask in one portion. Under nitrogen, the resulting mixture was heated to 80° C. and stirred for about 30 min before being further heated to 110° C. The reaction mixture slowly turned from yellowish to dark brown in color. After 4 h at 110° C., HPLC analysis indicated that compound 2 had been consumed. The heating was discontinued and the reaction mixture solidified as it was cooled.

After the mixture cooled to about 35° C., water (3000 mL) and EtOAc (2500 mL) were added and the mixture was vigorously stirred until all solids dissolved. The two layers were separated and the aqueous layer was further extracted with EtOAc (2500 mL). The organic layers were combined, washed sequentially with 1 N aq. HCl solution (500 mL), sat. aq. NaHCO₃ (500 mL), and brine (300 mL) before being dried over Na₂SO₄ and concentrated under reduced pressure. Crude 7-(1-bromoethyl)-3-methyl-5H-thiazolo[3,2-a]pyrimidin-5-one (4, 538.5 g, 56% for two steps, 90% pure by HPLC analysis) was obtained as a yellowish solid, which was used in the subsequent reaction without further purification. ¹H NMR (400 MHz, DMSO-d₆) δ 7.05 (m, 1H), 6.27 (s, 1H), 5.17 (q, J=6.9 Hz, 1H), 2.65 (s, 3H), 1.85 (d, J=6.9 Hz, 3H); LCMS calc. for $C_9H_{10}BrN_2OS$ $(M+H)^+$: m/z 274.96, 272.96. Found: 274.75, 272.75.

Step 3. 6-Bromo-7-(1-bromoethyl)-3-methyl-5H-thiazolo[3,2-a]pyrimidin-5-one

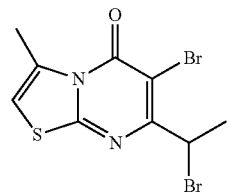

5

Under nitrogen, a suspension of crude 7-(1-bromoethyl)-3-methyl-5H-thiazolo[3,2-c]pyrimidin-5-one (4, 538.5 g, 1971 mmol) in MeCN (3000 mL) was stirred at room temperature until a clear solution was obtained. N-Bromosuccinimide (421.1 g, 2366 mmol, 1.2 eq.) was then added in portions via a powder funnel at room temperature. Precipitate formed upon addition of NBS and the reaction temperature rose to about 46° C. The resulting reaction mixture was heated to 50° C. and stirred for ~20 min. When HPLC indicated the reaction was complete, the reaction mixture was cooled to room temperature. A solution of Na₂SO₃ (149.1 g, 1183 mmol) in water (1500 mL) was added to the reaction mixture in portions and the resulting mixture was stirred at room temperature for ~20 min before water (6000 mL) was added via an addition funnel. The stirring was continued for an additional 30 min. The precipitates were collected by filtration, washed with water (2×1 L), and dried to afford crude 6-bromo-7-(1-bromoethyl)-3-methyl-5H-thiazolo[3,2-a]pyrimidin-5-one (5, 543.3 g, 78.3%, 91.9% pure by HPLC analysis) as an off-white solid, which was used in the subsequent reaction without further purification. ¹H NMR (400 MHz, DMSO-d₆) δ 7.15 (q, J=1.3 Hz, 1H), 5.51 (q, J=6.7 Hz, 1H), 2.66 (d, J=1.2 Hz, 3H), 1.90 (d, J=6.7 Hz, 3H); LCMS calc. for $C_9H_9Br_2N_2OS$ $(M+H)^+$: m/z 352.87, 354.87. Found: 352.65, 354.60.

Step 4. 7-(1-Azidoethyl)-6-bromo-3-methyl-5H-thiazolo[3, 2-a]pyrimidin-5-one

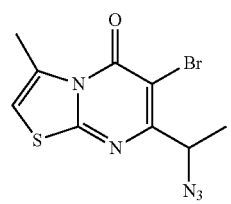

6

A suspension of 6-bromo-7-(1-bromoethyl)-3-methyl-5H-thiazolo[3,2-a]pyrimidin-5-one (5, 543.3 g, 1.54 mol) in DMF (2 L) was treated with NaN₃ (115 g, 1.77 mol, 1.15 eq.) in small portions via a powder funnel at room temperature. After 5-min, the mixture turned to a clear solution. The resulting solution was stirred at room temperature for about 1-2 h. When HPLC and LCMS indicated ~5% starting material remaining, an additional portion of NaN₃ (25.08 g, 0.39 mol, 0.25 eq.) was added and the stirring was continued. After a total of 2.5 h, HPLC analysis indicated the reaction was complete. A 5% aq. NaHCO₃ solution (5 L) was then added via an addition funnel over a 30-min period and the resulting suspension was stirred at room temperature for 1 h. The resulting precipitates were collected by filtration, washed with water (2×1 L), and dried to afford crude 7-(1-azidoethyl)-6-bromo-3-methyl-5H-thiazolo[3,2-a]pyrimidin-5-one (6, 492.9 g, >99% yield, 98.1% pure by HPLC analysis) as an off-white solid, which was used for the subsequent reaction without further purification. ¹H NMR (400 MHz, DMSO-d₆) δ 7.15 (q, J=1.3 Hz, 1H), 4.83 (q, J=6.8 Hz, 1H), 2.67 (d, J=1.4 Hz, 3H), 1.48 (d, J=6.8 Hz, 3H); LCMS calc. for $C_9H_9BrN_5OS$ $(M+H)^+$: m/z 313.96, 315.96.

Found: 313.75, 315.75.

Step 5. (+)-7-(1-Aminoethyl)-6-bromo-3-methyl-5H-thiazolo[3, 2-a]pyrimidin-5-one

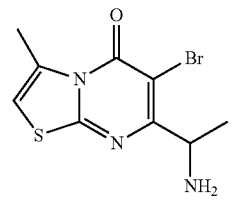

7

Method A

A suspension of crude 7-(1-azidoethyl)-6-bromo-3-methyl-5H-thiazolo[3,2-a]pyrimidin-5-one (6, 484.8 g, 1543 mmol) and NaI (1320.8 g, 8811.5 mmol, 5.71 eq.) in MeOH (1520 mL) was stirred at room temperature for 10 min. A freshly prepared solution of chlorotrimethylsilane (TMSCl, 743 mL, 5850 mmol, 3.8 equiv) in MeOH (262 mL) was added while maintaining the internal reaction mixture temperature at lower than 60° C. After the addition of TMSCl, solids in the reaction mixture slowly dissolved and the reaction mixture turned black. The stirring was continued for 30 min. Upon completion of the reaction (monitored by HPLC), a solution of Na₂SO₃ (583.51 g, 4629.4 mmol) in water (2500 mL) was added to the reaction mixture at room temperature. The dark color of the reaction mixture faded and white solids precipitated from the mixture. The reaction mixture (pH ~7) was cooled with an ice-water bath and a 50% aq. solution of NaOH (225 mL) was added drop-wise with stirring to adjust the pH to about 12. EtOAc (4 L) was added and stirring was continued for about 20 min. The two layers were separated and the aqueous layer was further extracted with additional EtOAc (4×1 L), with NaCl (500 g) added to aqueous layer during the last extraction. The organic extracts were combined and extracted with 2 N aq. HCl (2×1.5 L). TLC indicated no product in organic layer after aqueous acid extraction. The two HCl extracts were then combined and cooled with an ice-water bath before being treated with a 50% aq. NaOH solution (200 mL) to adjust the pH to ~12. The mixture was then stirred at 0° C. for ~30 min and solids slowly precipitated from the mixture. The precipitates were collected by filtration, washed with water (500 mL), and dried to afford a first crop of the crude title product (7, 248 g) as an off-white solid. The filtrate was extracted with EtOAc three times (3×1 L) and the organic extracts were combined, dried over $Na_2SO_4$, and concentrated under reduced pressure to afford a second crop of the crude desired product (7, 92 g) as an off-white solid. The two crops were combined to afford crude (+)-7-(1-aminoethyl)-6-bromo-3-methyl-5H-thiazolo[3,2-a]pyrimidin-5-one (7, 340 g, 76%, >99% pure by HPLC analysis) as an off-white solid, which was used without further purification. $^1$H NMR (400 MHz, DMSO-$d_6$) 7.08 (q, J=1.3 Hz, 1H), 4.19 (q, J=6.7 Hz, 1H), 2.65 (d, J=1.3 Hz, 3H), 1.17 (d, J=6.7 Hz, 3H); LCMS calc. for $C_9H_{11}BrN_3OS$ (m+h)$^+$: m/z 287.97, 289.97. Found: 287.75, 289.75.

Method B

A suspension of crude 7-(1-azidoethyl)-6-bromo-3-methyl-5H-thiazolo[3,2-a]pyrimidin-5-one (6, 22.6 g, 71.9 mmol) in MeOH (200 mL) was treated with NaI (64.7 g, 432 mmol, 6.0 eq.) at room temperature and the resulting mixture was stirred for 10 min. A freshly prepared solution of chlorotrimethylsilane (TMSCl, 55 mL, 432 mmol, 6.0 eq.) in MeOH (29 mL) was then added while maintaining the internal temperature of the reaction mixture at lower than 60° C. The solids in the reaction mixture slowly dissolved and the mixture turned dark. When HPLC showed that the reaction was complete, a solution of $Na_2SO_3$ (69.4 g, 439 mmol) in water (259 mL) was added to the reaction mixture at room temperature. The dark color of the reaction mixture faded and a white solid precipitated from the reaction mixture. The reaction mixture (pH ~3) was then cooled with an ice-water bath before a 3 N aq. solution of NaOH (85 mL) was added drop-wise with stirring to adjust the pH to ~11. Di-tert-butyl dicarbonate ($Boc_2O$, 28.3 g, 129 mmol, 1.80 eq.) was added and the reaction mixture was stirred at room temperature for 2 h. An additional portion $Boc_2O$ (10.0 g, 45.8 mmol, 0.64 eq.) was added, followed by 3 N aq. solution of NaOH (15 mL). The reaction mixture was stirred at room temperature for an additional 30 min, at which time HPLC analysis indicated the reaction was complete. The reaction mixture was then extracted with EtOAc (3×150 mL) and the combined extracts were washed with brine, dried over anhydrous $Na_2SO_4$, filtered, and concentrated under reduced pressure to yield an oily residue. The oily residue was treated with a solution of 4 N HCl in 1,4-dioxane (206 mL) at room temperature and the resulting mixture was stirred at room temperature for 1.5 h. Solids precipitated from the mixture and HPLC analysis indicated completion of the reaction. The solids were collected by filtration, washed with MTBE, and dried on the filter under vacuum for 1 h to afford the corresponding crude amine hydrochloride salt (7, 25.1 g) as a purple powder. The crude amine hydrochloride salt (7) was dissolved in water (50 mL) at room temperature and the resulting solution was cooled to 0-5° C. A 50% aq. solution of NaOH (~5 mL) was added to the solution to adjust the pH to about 11. The resulting mixture was warmed to room temperature and stirred at room temperature for 20 min. The precipitates were collected by filtration, washed with water (10 mL), and dried on the filter under vacuum for 18 h to afford crude (+)-7-(1-aminoethyl)-6-bromo-3-methyl-5H-thiazolo[3,2-a]pyrimidin-5-one (7, 18.8 g, 90.7% yield) as an off-white solid which was used without further purification.

Intermediate 2. 6-Chloro-9-(tetrahydro-2H-pyran-2-yl)-9H-purine (17)

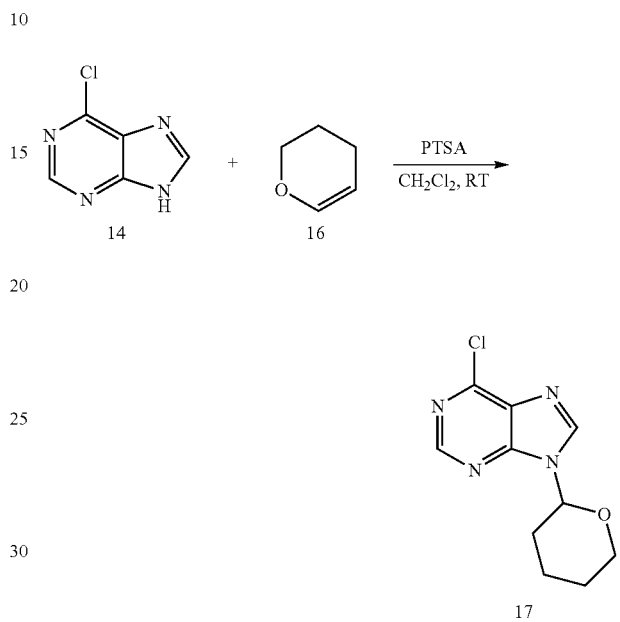

A suspension of 6-chloropurine (14, 40.0 g, 90.6 mmol), p-toluenesulfonic acid monohydrate (0.5 g, 2.63 mmol, 0.03 eq.), and 3,4-dihydro-2H-pyran (16, 35.4 mL, 136 mmol, 1.5 eq.) in DCM (400 mL) was stirred at room temperature for 3 h to give a slightly hazy solution. When HPLC analysis indicated the presence of <0.1% purine 14, a 2.5% aq. $Na_2CO_3$ solution (200 mL) was added to the reaction mixture and the resulting mixture was stirred at room temperature for 15 min. The two layers were separated and the organic layer was treated with additional 2.5% aq. $Na_2CO_3$ (200 mL). The two layers were separated and the organic layer was dried over $Na_2SO_4$. The mixture was filtered and the resulting solid cake was rinsed with DCM (20 mL). The filtrate was concentrated to a minimal volume under reduced pressure at 35° C. n-Heptane (200 mL) was added to the concentrated filtrate and the mixture was stirred vigorously at room temperature until a solid suspension formed (up to 16 h). The precipitate was collected by filtration, rinsed with n-heptane (100 mL), and dried at 40° C. under vacuum to afford crude 6-chloro-9-(tetrahydro-2H-pyran-2-yl)-9H-purine (17, 55.5 g, 89.8%) as a pale yellow solid, which was used without further purification. $^1$H NMR (300 MHz, DMSO-$d_6$) δ 8.90 (s, 1H), 8.79 (s, 1H), 5.78 (d, J=10.9 Hz, 1H), 3.99 (m, 1H), 3.70 (m, 1H), 2.31 (m, 1H), 1.99 (m, 2H), 1.74 (m, 1H), 1.58 (m, 2H); LCMS calc. for $C_{10}H_{12}ClN_4O$ (M+H)$^+$: 239.04. Found: 239.1.

Example 1. (S)-7-(1-((9H-purin-6-yl)amino)ethyl)-6-(3-fluorophenyl)-3-methyl-5H-thiazolo[3,2-a]pyrimidin-5-one

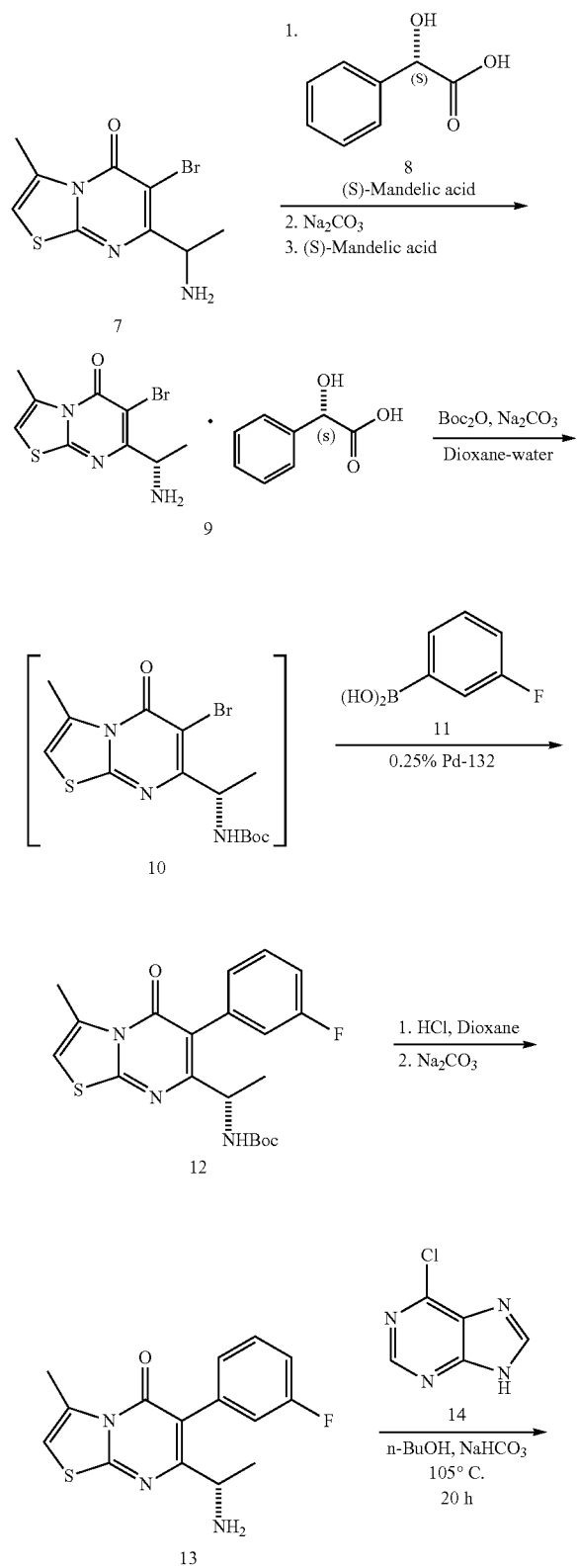

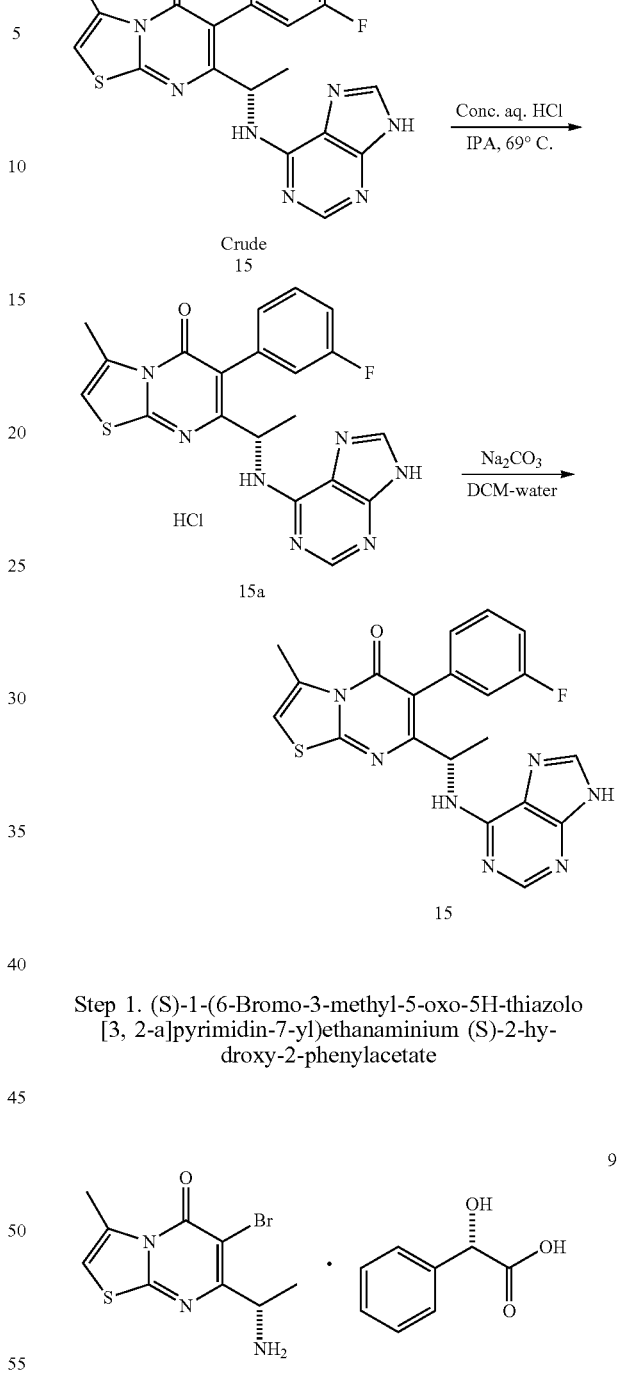

Step 1. (S)-1-(6-Bromo-3-methyl-5-oxo-5H-thiazolo[3,2-a]pyrimidin-7-yl)ethanaminium (S)-2-hydroxy-2-phenylacetate

9

A suspension of 7-(1-aminoethyl)-6-bromo-3-methyl-5H-[1,3]thiazolo[3,2-a]pyrimidin-5-one (7, 400.0 g, 1.388 mol) in IPA (8 L) was heated to reflux to afford a clear solution. The solution was treated with a solution of (S)-(+)-mandelic acid (8, 105.6 g, 0.694 mol, 0.5 eq.) in IPA (3.5 L) over a 20 min period at reflux. The resulting mixture was then cooled to about 30° C. The precipitate was collected by filtration, rinsed with IPA (200 mL), and dried overnight on the filter under vacuum to afford a first crop of the chiral resolution product (265.2 g, 95.82% e.e. by chiral HPLC) as a white solid. The collected solids (265.2 g, 0.598 mol) were mixed with a solution of Na₂CO₃ (110 g, 1.0 mol) in water (1900 mL) and stirred at room temperature for 30 min. The pH of the solution was about 9-10. The solids were collected by filtration, rinsed with water (200 mL), and dried on the filter under vacuum for 2 h to afford the enantiomerically enriched free amine (293 g) as a slightly wet cake. The wet cake was then dissolved in IPA (5 L) at reflux and the resulting solution was treated with a solution of (S)-(+)-mandelic acid (91.0 g, 0.598 mol, 1.0 equiv) in IPA (1 L) at reflux over a 10 min period. The reaction mixture turned clear and precipitate formed at ~79° C. The mixture was then cooled to room temperature and stirred at room temperature overnight. The precipitates were collected by filtration, rinsed with IPA (300 mL), and dried on the filter under vacuum for 4 h to afford (S)-1-(6-bromo-3-methyl-5-oxo-5H-thiazolo[3,2-a]pyrimidin-7-yl)ethanaminium (S)-2-hydroxy-2-phenylacetate (9, 237.5 g, 77.8% yield, >99.6% ee by chiral HPLC) as a white solid. ¹H NMR (400 MHz, DMSO-d₆) δ 7.33 (d, J=7.5 Hz, 2H), 7.22 (dd, J=7.1, 7.5 Hz, 2H), 7.16 (m, 2H), 4.61 (s, 1H), 4.47 (q, J=6.9 Hz, 1H), 2.68 (d, J=1.1 Hz, 3H), 1.31 (d, J=6.8 Hz, 3H). LCMS calc. for C₉HiiBrN₃OS (M+H)⁺ for the free base: m/z 289.97, 287.97. Found: 289.75, 287.75. X-ray crystallography of compound 9 confirmed the chiral amine having an S-configuration.

Step 2. (S)-tert-butyl (1-(6-(3-fluorophenyl)-3-methyl-5-oxo-5H-thiazolo[3,2-a]pyrimidin-7-yl)ethyl) carbamate

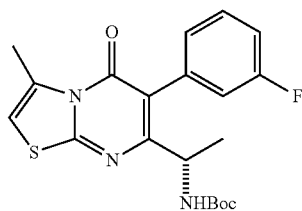

12

A 2-L, three-necked, round-bottomed flask was charged with (S)-1-(6-bromo-3-methyl-5-oxo-5H-thiazolo[3,2-a]pyrimidin-7-yl)ethanaminium (S)-2-hydroxy-2-phenylacetate (9, 40.0 g, 90 mmol), Na₂CO₃ (33.6 g, 318 mmol, 3.5 eq.), 1,4-dioxane (120 mL), and water (6.0 mL). With stirring, Boc₂O (21.8 g, 99.8 mmol, 1.1 eq.) was added in one portion. The resulting mixture was stirred at room temperature for 1 h, at which time HPLC analysis indicated the complete consumption of the starting material. The reaction flask was fitted with a condenser equipped with a nitrogen inlet, consisting of a T-tube assembly connected to a mineral oil bubbler. 3-Fluorophenyl boronic acid (11, 16.5 g, 118 mmol, 1.30 eq.) was added and the resulting mixture was degassed with a steam of nitrogen for 10 min. Dichloro(bis{di-tert-butyl[4-(dimethylamino)phenyl]phosphoranyl}) palladium (Pd-132, 160 mg, 0.23 mmol, 0.0025 eq.) was added and the nitrogen degassing was continued for 10 min. The mixture was then heated to reflux and stirred for 4 h. When HPLC analysis showed that the coupling reaction was complete, the reaction mixture was a clear solution with white precipitate at the bottom of the flask. The heating was discontinued and the reaction mixture was cooled to ~80° C. Water (600 mL) was then added to the reaction mixture at ~80° C. with stirring. The mixture was then cooled to room temperature and stirred for 22 h. Solids slowly precipitated from the mixture, yielding a suspension. The precipitates were collected by filtration, washed with water (3×10 mL), and dried to afford (S)-tert-butyl 1-(6-(3-fluorophenyl)-3-methyl-5-oxo-5H-thiazolo[3,2-a]pyrimidin-7-yl)ethylcarbamate (12, 36.1 g, 98.4%) as an off-white solid. ¹H NMR (500 MHz, DMSO-d₆) δ 7.48 (ddd, J=8.1, 7.8, 6.2 Hz, 1H), 7.18 (m, 3H), 7.05 (q, J=1.3 Hz, 1H), 6.96 (d, J=7.5 Hz, 1H), 4.41 (m, 1H), 2.66 (d, J=1.3 Hz, 3H), 1.33 (s, 9H), 1.13 (d, J=6.8 Hz, 3H); LCMS calc. for C₂₀H₂₃FN₃O₃S (M+H)⁺: m/z 404.1. Found 404.1.

Step 3. (S)-7-(1-Aminoethyl)-6-(3-fluorophenyl)-3-methyl-5H-thiazolo[3, 2-a]pyrimidin-5-one

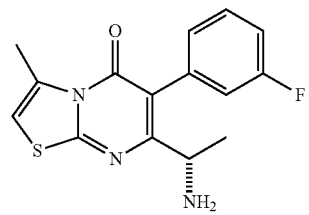

13

A mixture of (S)-tert-butyl 1-(6-(3-fluorophenyl)-3-methyl-5-oxo-5H-thiazolo[3,2-a]pyrimidin-7-yl)ethylcarbamate (12, 144.0 g, 357 mmol) and 4.0 M HCl in 1,4-dioxane (929 mL, 3.716 mol, 10.4 equiv) was stirred at room temperature for 45 min. When HPLC analysis indicated the amine deprotection reaction was complete, water (1000 mL) was added and the resulting mixture was cooled with an ice-water bath. A solution of Na₂CO₃ (315 g, 2.97 mol) in water (1000 mL) was added until the pH reached ~10. The reaction mixture was then extracted twice with EtOAc (2.0 L and 0.5 L). The organic extracts were combined, washed with brine, dried over Na₂SO₄, and concentrated under reduced pressure to afford (S)-7-(1-aminoethyl)-6-(3-fluorophenyl)-3-methyl-5H-thiazolo[3,2-a]pyrimidin-5-one (13, 103.1 g, 95.2%) as a yellowish solid. ¹H NMR (400 MHz, DMSO-d₆) δ 7.45 (ddd, J=8.1, 7.9, 5.9 Hz, 1H), 7.19 (m, 1H), 7.12 (m, 2H) 7.04 (q, J=1.1 Hz, 1H), 3.57 (q, J=6.6 Hz, 1H), 2.64 (d, J=1.3 Hz, 3H), 1.8 (br s, 2H), 1.10 (d, J=6.7 Hz, 3H); LCMS calc. for C₁₅H₁₅FN₃OS (M+H)+: m/z 304.08. Found: 303.9.

Step 4. (S)-7-(1-(9H-Purin-6-ylamino)ethyl)-6-(3-fluorophenyl)-3-methyl-5H-thiazolo[3, 2-a]pyrimidin-5-one (Crude Product)

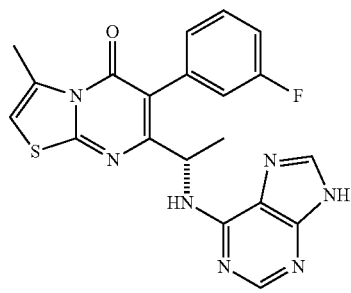

15

In a 12-L, three-necked round-bottomed flask fitted with a mechanical stirrer, a J-KEM temperature controller, and a refluxing condenser fitted with a nitrogen inlet, was charged (S)-7-(1-aminoethyl)-6-(3-fluorophenyl)-3-methyl-5H-thiazolo[3,2-a]pyrimidin-5-one (13, 94.3 g, 311 mmol), 6-chloropurine (14, 62.4 g, 404 mmol, 1.3 eq.), NaHCO$_3$ (26.4 g, 311 mmol, 1.0 eq.), and 1-BuOH(1886 mL) at room temperature. The mixture was degassed with nitrogen for 5-10 min before being heated to an internal temperature of about 105° C. under nitrogen. The reaction mixture was then stirred at about 105° C. for 3 h, at which time HPLC analysis showed ~9.0% of the starting material (13) remaining in the reaction mixture. N,N-Diisopropylethylamine (DIPEA, 6.0 mL, 34 mmol, 0.11 eq.) was added to the reaction mixture via a syringe at about 105° C. and heating was continued for an additional 16 h. When HPLC analysis indicated the starting material 13 was completely consumed, the heating was discontinued and the reaction mixture was cooled to room temperature. Water (500 mL) was added to the reaction mixture and the resulting mixture was concentrated under reduced pressure to yield a greenish semi-solid. The resulting semi-solid was treated with DCM (1200 mL) and MeOH (60 mL) and the resulting solution was washed with 2.5% aq. Na$_2$CO$_3$ solution (2×600 mL). The combined aqueous layers were then extracted with DCM (500 mL) and the combined organic extracts were washed with brine (300 mL), dried over Na$_2$SO$_4$, and concentrated under reduced pressure to afford the crude title product as a brownish foam (Yield: ~105 g).

Step 5. (S)-7-(1-(9H-Purin-6-ylamino)ethyl)-6-(3-fluorophenyl)-3-methyl-5H-thiazolo[3, 2-a]pyrimidin-5-one hydrochloride salt (Crude HCl Salt)

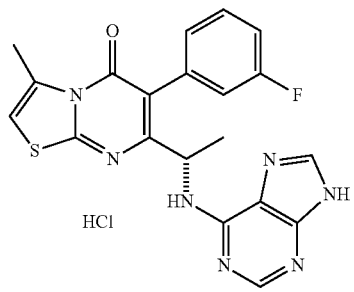 [SMILES: Cc1csc2nc([C@H](C)Nc3ncnc4[nH]cnc34)c(-c3cccc(F)c3)c(=O)n12 ; Cl]

The crude product from Step 4 was dissolved in IPA (3000 mL) and the resulting solution was heated to 68° C. before a solution of 12.0 M conc. aq. HCl (28.5 mL, 342 mmol, 1.10 eq.) in IPA (180 mL) was added at 68° C. over a period of 10 min. The resulting clear solution was stirred at about 69° C. for 15 min before being cooled to room temperature. Solids started to precipitate at ~65° C. The mixture was then stirred at room temperature for 3 h. The precipitates were collected by filtration, rinsed with IPA (120 mL) and dried on the filter under vacuum for 2 days to afford the crude HCl salt of compound 15 as a yellowish solid.

Step 6. (S)-7-(1-(9H-Purin-6-ylamino)ethyl)-6-(3-fluorophenyl)-3-methyl-5H-thiazolo[3, 2-a]pyrimidin-5-one (Purified Product)

A suspension of the crude hydrochloride salt from Step 5 in DCM (1000 mL) was treated with a 10% aq. Na$_2$CO$_3$ solution at room temperature. The resulting mixture was stirred at room temperature until the pH reached ~9-10. The two layers were separated and the aqueous layer was extracted with DCM (100 mL). The combined DCM extracts were washed with brine, dried over Na$_2$SO$_4$, and filtered. The filtrate was then charged with MeOH (30 mL) and EtOAc (1360 mL) and the resulting mixture was distilled at atmospheric pressure. The resulting residue was then cooled to room temperature and subsequently to 0-5° C. and stirred at 0-5° C. for 1 h. The precipitates were collected by filtration, rinsed with cold EtOAc (100 mL), and dried overnight on the filter under vacuum to afford (S)-7-(1-(9H-purin-6-ylamino)ethyl)-6-(3-fluorophenyl)-3-methyl-5H-thiazolo[3,2-a]pyrimidin-5-one (15, 79 g, 60%). $^1$H NMR (400 MHz, CDCl$_3$) δ 14.15 (br s, 1H), 8.33 (s, 1H), 7.94 (s, 1H), 7.40 (m, 1H), 7.15-7.07 (m, 3H), 6.81 (d, J=8.4 Hz, 1H), 6.41 (d, J=1.2 Hz, 1H), 5.46 (br s, 1H), 2.74 (d, J=1.1 Hz, 3H), 1.42 (d, J=6.7 Hz, 3H); $^{13}$C NMR (100 MHz, CDCl$_3$) δ 163.9, 163.0 ($^1J_{CF}$=246.3 Hz), 162.3, 161.5, 153.8, 152.2, 149.9, 138.5, 137.0, 135.3 ($^3J_{CF}$=7.9 Hz), 130.2 ($^3J_{CF}$=8.4 Hz), 126.5 ($^4J_{CF}$=2.4 Hz), 119.7, 117.9 ($^2J_{CF}$=21.6 Hz), 116.5, 115.2 ($^2J_{CF}$=20.9 Hz), 106.4, 47.5, 21.1, 18.7; $^{19}$F NMR (376 MHz, CDCl$_3$) δ-113.3. LCMS calc. for C$_{20}$H$_{17}$FN$_7$OS (M+H)$^+$: m/z 422.1. Found: 422.0. Enantiomeric excess (ee): >99% by chiral HPLC.

Example 2. Alternate preparation of (S)-7-(1-((9H-purin-6-yl)amino)ethyl)-6-(3-fluorophenyl)-3-methyl-5H-thiazolo[3,2-a]pyrimidin-5-one

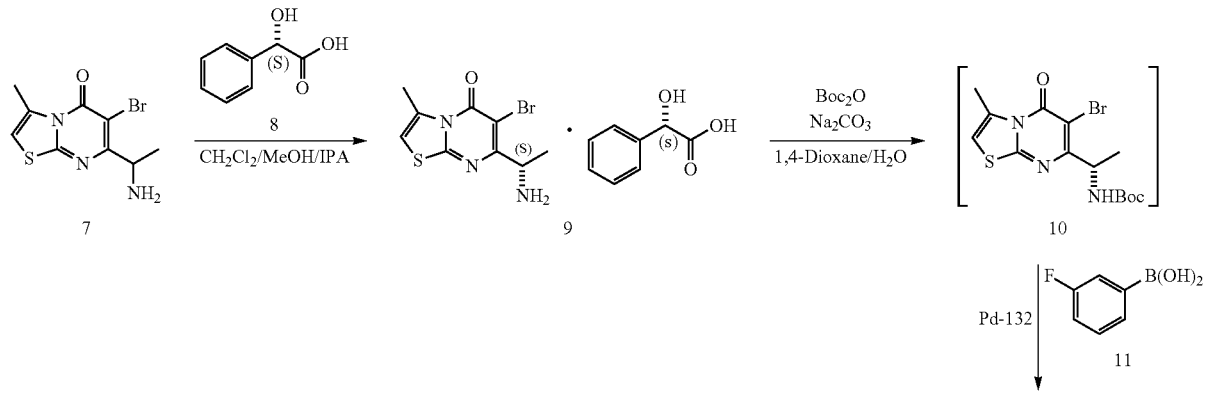

-continued

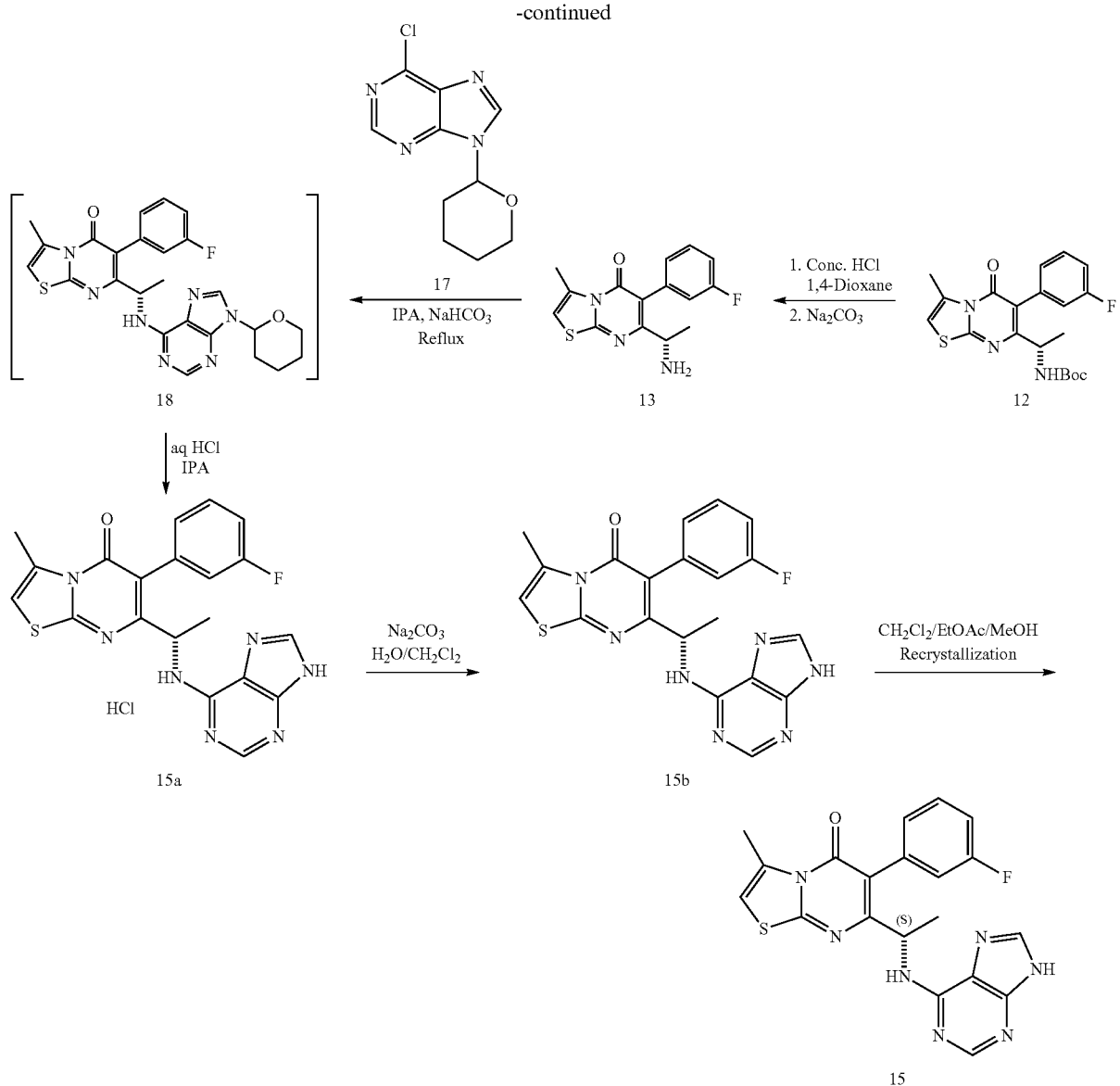

Step 1. (S)-1-(6-Bromo-3-methyl-5-oxo-5H-thiazolo[3,2-a]pyrimidin-7-yl)ethanaminium (S)-2-hydroxy-2-phenylacetate

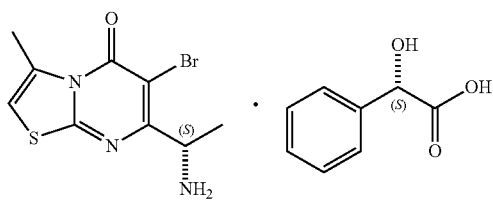

A clean and dry reactor equipped with an overhead stirrer, a thermocouple, and a nitrogen inlet was purged with nitrogen and the nitrogen flow was maintained thereafter. 7-(1-Aminoethyl)-6-bromo-3-methyl-5H-[1,3]thiazolo[3,2-a]pyrimidin-5-one (7, 1000 g, 3.47 mol) and DCM (13.0 L) were charged to the reactor. The mixture was heated to about 30° C. and stirred until a clear solution was obtained. S-(+)-Mandelic acid (8, 264 g, 1.74 mol, 0.50 eq.) was then charged into the reactor. The resulting suspension was heated at reflux (~40° C.) for at least 1 h. The reaction mixture was cooled to about 25° C. over a 1 h period and was stirred at 25° C. for at least 1 hour. The reaction mixture was then filtered and the filter cake was washed twice with DCM (2×2.5 L). The wet cake was charged back to the reactor, MeOH (6.1 L) was added, and the mixture was distilled at atmospheric pressure. When the distillation was stopped, the batch was cooled to below 50° C. Isopropanol (IPA, 9.1 L) was then charged into the reactor and the resulting mixture was heated at gentle reflux (~70° C.) for at least 3 h. The mixture was then cooled to 25° C. over a period of at least 3 h. The precipitates were collected by filtration, washed with a mixture of MeOH/IPA (1:1, 4×1.0 L), and dried under vacuum at below 50° C. to a loss on drying (LOD) of ≤1% to afford (S)-1-(6-bromo-3-methyl- 5-oxo-5H-thiazolo[3,2-a]pyrimidin-7-yl)ethanaminium (S)-2-hydroxy-2-phenylacetate (9, 672 g, 44%) as an off-white solid. $^1$H NMR (400 MHz, DMSO-$d_6$) δ 7.33 (d, J=7.5 Hz, 2H), 7.22 (dd, J=7.1, 7.5 Hz, 2H), 7.16 (m, 2H), 4.61 (s, 1H), 4.47 (q, J=6.9 Hz, 1H), 2.68 (d, J=1.1 Hz, 3H), 1.31 (d, J=6.8 Hz, 3H). LCMS calc. for $C_9H_{11}BrN_3OS$ (free base) (M+H)$^+$: m/z 289.97, 287.97. Found: 289.75, 287.75. Chiral purity: >99.5% by chiral HPLC.

Step 2. (S)-tert-butyl (1-(6-(3-fluorophenyl)-3-methyl-5-oxo-5H-thiazolo[3,2-a]pyrimidin-7-yl)ethyl) carbamate (12)

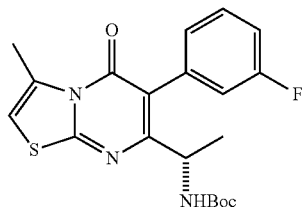

12

A clean and dry reactor equipped with an overhead stirrer, a thermocouple, a reflux condenser, and a nitrogen inlet was purged with nitrogen and the nitrogen flow was maintained thereafter. Dioxane (10 L), (S)-1-(6-bromo-3-methyl-5-oxo-5H-thiazolo[3,2-a]pyrimidin-7-yl)ethanaminium (S)-2-hydroxy-2-phenylacetate (9, 1000 g, 2.27 mol, 1.0 eq.), water (2.9 L), and $Na_2CO_3$ (842 g, 7.95 mol, 3.5 eq.) were charged into the reactor sequentially with stirring. $Boc_2O$ (545 g, 2.50 mol, 1.1 eq.) was then added to the reaction mixture in portions. The resulting reaction mixture was stirred at about 30° C. for at least 4 h and the reaction progress was monitored by HPLC analysis. When HPLC analysis showed the completion of the amine protection reaction, 3-fluorophenylboronic acid (11, 413 g, 2.95 mol, 1.3 eq.) was charged to the reaction mixture. The resulting reaction mixture was degassed by pulling a vacuum and purging with nitrogen two times with stirring. Dichloro(bis{di-tert-butyl[4-(dimethylamino)phenyl]-phosphoranyl})palladium (Pd-132, 4.0 g, 5.7 mmol, 0.0025 eq.) was added to the mixture and the resulting reaction mixture was degassed before being heated to a gentle reflux (~85° C.) and stirring at reflux for at least 3 h. When HPLC analysis showed the completion of the Suzuki coupling reaction, the mixture was cooled to 50° C. and subsequently distilled under reduced pressure until 6000-8000 mL remained. Toluene (5.0 L) was then added to the mixture and distillation was resumed under reduced pressure until 600-800 mL remained. Toluene (15 L) and water (10 L) were added to the mixture, which was then stirred at 35° C. for 30 min. The two layers were allowed to separate and the aqueous layer was removed. Water (5 L) was charged into the reactor and the mixture was stirred for 20 min. The two layers were allowed to separate, and the aqueous layer was removed. A 20% aq. $NaHSO_3$ solution (10 L) was added to the organic layer and the mixture was heated to about 50° C. and stirred for at least 2 h. The layers were allowed to separate, and the aqueous layer was removed. The washing process was repeated once with 20% aq. $NaHSO_3$ (10 L). Anhydrous $Na_2SO_4$ (1.0 kg) was added to the organic layer and the mixture was agitated for at least 30 min. Thiol silica (0.2 kg) was then added to the reactor and the resulting mixture was heated to 50° C. and stirred for at least 2 h. The mixture was then cooled to about 25° C. and the solids were filtered off. The reactor was washed with toluene (3.0 L) and the wash was transferred onto the filter to wash the solids. The combined filtrate and toluene wash were transferred into a clean reactor and the solution was concentrated under reduced pressure at below 50° C. until about 3.5-4.5 L remained. The remaining solution was heated at ~80° C. for at least 20 min and n-heptane (3.5 L) was added. The resulting mixture was heated at about 85° C. for at least 30 min, cooled to about 20° C. over a period of at least 1 h, and stirred for at least 30 min. The resulting solids were collected by filtration and washed with n-heptane (2.0 L). The wet product was dried under vacuum at 50° C. to a loss of drying (LOD)<1.0% to afford (S)-tert-butyl 1-(6-(3-fluorophenyl)-3-methyl-5-oxo-5H-thiazolo[3,2-a]pyrimidin-7-yl)ethylcarbamate (12, 870 g, 95% yield) as a white solid. $^1$H NMR (500 MHz, DMSO-$d_6$) δ 7.48 (ddd, J=8.1, 7.8, 6.2 Hz, 1H), 7.18 (m, 3H), 7.05 (q, J=1.3 Hz, 1H), 6.96 (d, J=7.5 Hz, 1H), 4.41 (m, 1H), 2.66 (d, J=1.3 Hz, 3H), 1.33 (s, 9H), 1.13 (d, J=6.8 Hz, 3H). LCMS calc. for $C_{20}H_{23}FN_3O_3S$ (M+H)$^+$: m/z 404.1. Found 404.1.

Step 3. (S)-7-(1-Aminoethyl)-6-(3-fluorophenyl)-3-methyl-5H-thiazolo[3, 2-a]pyrimidin-5-one (13)

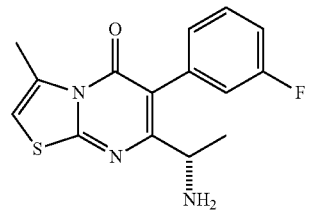

13

A clean and dry reactor equipped with an overhead stirrer, a thermocouple, and a nitrogen inlet was purged with nitrogen and the nitrogen flow was maintained thereafter. Dioxane (2.5 L) and (S)-tert-butyl 1-(6-(3-fluorophenyl)-3-methyl-5-oxo-5H-thiazolo[3,2-a]pyrimidin-7-yl)ethylcarbamate (12, 1000 g, 2.48 mol) were added to the reactor and the resulting slurry was stirred. Water (1.7 L) was then added and the resulting mixture was cooled to below 20° C. Concentrated aq. HCl ($^{37}$%, 1.65 L, 19.8 mol, 8 eq.) was added to the reactor while maintaining an internal temperature at below 30° C. The reaction mixture was stirred for at least 2 h at 25° C. When HPLC analysis showed the completion of the amine deprotection reaction, DCM (10 L) was added to the reactor and the mixture was cooled to 10° C. A solution of $Na_2CO_3$ (1708 g, 16.1 mol, 6.5 eq.) in water (15 L) was then added with stirring over a period of 20 min while the internal temperature was maintained at below 20° C. The mixture was stirred for an additional 10 min and the pH maintained at above 9. Stirring was then stopped and the layers were allowed to separate. The organic layer was collected, and the aqueous layer was washed with additional DCM (2.0 L) and stirred for at least 10 min. The two layers were allowed to separate and the organic layer was collected. The two DCM extracts were combined, washed twice with 10% aq. NaCl (2×5.0 L), and dried over anhydrous $Na_2SO_4$ (1000 g). The solids were filtered off and the filter cake was rinsed with DCM (2.0 L). The filtrate and wash were transferred into a clean reactor and concentrated under reduced pressure at 30-50° C. until minimal volume remained. n-Heptane (5.0 L) was added to the concentrated mixture, and the resulting mixture was concentrated under reduced pressure at 30-50° C. until minimal volume remained. Additional n-Heptane (5.0 L) was added and the resulting mixture was heated at 80° C. for at least 30 min, cooled to 20° C. over a period of at least 1 h, and stirred at 20° C. for 30 min. The resulting solids were collected by filtration and the resulting filter cake was washed with n-heptane (2.0 L). The wet cake was dried under reduced pressure at ≤50° C. until the loss of drying (LOD) was ≤0.5% to afford (S)-7-(1-aminoethyl)-6-(3-fluorophenyl)-3-methyl-5H-thiazolo[3,2-a]pyrimidin-5-one (13, 714 g, 95%) as an off-white solid. $^1$H NMR (400 MHz, DMSO-d$_6$) δ 7.45 (ddd, J=8.1, 7.9, 5.9 Hz, 1H), 7.19 (m, 1H), 7.12 (m, 2H) 7.04 (q, J=1.1 Hz, 1H), 3.57 (q, J=6.6 Hz, 1H), 2.64 (d, J=1.3 Hz, 3H), 1.8 (br s, 2H), 1.10 (d, J=6.7 Hz, 3H). LCMS calc. for $C_{15}H_{15}FN_3OS$ (M+H)$^+$: m/z 304.08.

Found: 303.9.

Step 4. (S)-7-(1-(9H-Purin-6-ylamino)ethyl)-6-(3-fluorophenyl)-3-methyl-5H-thiazolo[3, 2-a]pyrimidin-5-one hydrochloride (15a)

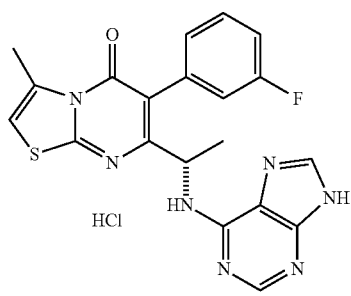

15a

A clean and dry reactor equipped with an overhead stirrer, a thermocouple, a reflux condenser, an addition funnel, and a nitrogen inlet was purged with nitrogen and the nitrogen flow was maintained thereafter. IPA (11 L), (S)-7-(1-aminoethyl)-6-(3-fluorophenyl)-3-methyl-5H-thiazolo[3,2-a]pyrimidin-5-one (13, 1000 g, 3.30 mol), 6-chloro-9-(tetrahydro-2H-pyran-2-yl)-9H-purine (17, 1023 g, 4.29 mol, 1.3 eq.), and NaHCO$_3$ (290 g, 3.45 mol, 1.05 eq.) were added to the reactor. The resulting reaction mixture was heated at gentle reflux (~82° C.) for at least 20 h. When HPLC analysis showed completion of the S$_N$2 reaction with <1% of compound 13 remaining, the reaction mixture was cooled to about 30° C. Aqueous conc. HCl ($^{37}$%, 0.85 L, 10.2 mol, 3.1 eq.) was added and the resulting mixture was stirred at 30° C. for at least 4 h. When HPLC analysis showed the completion of the N-THP deprotection (<1% compound 18 remaining), the mixture was cooled to 10° C. and stirred for at least 2 h. The solids were collected via filtration and the resulting filter cake was washed three times with IPA (3×1.0 L) to afford a wet cake of salt 15a (>1511 g,). The wet cake was used directly for next step without further drying.

Step 5. (S)-7-(1-(9H-Purin-6-ylamino)ethyl)-6-(3-fluorophenyl)-3-methyl-5H-thiazolo[3, 2-a]pyrimidin-5-one (Crude Free Base in DCM)

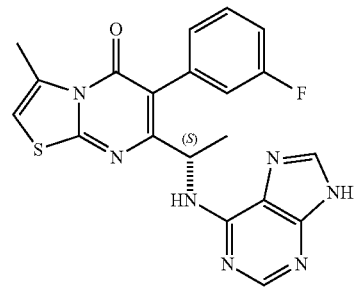

15b

A clean reactor equipped with an overhead stirrer, a thermocouple, a reflux condenser, an addition funnel, and a nitrogen inlet was purged with nitrogen, and a nitrogen flow was maintained thereafter. Water (10 L) and Na$_2$CO$_3$ (700 g, 6.60 mol, 2.0 eq.) were added to the reactor and the mixture was stirred until a solution was achieved. DCM (15.0 L) and crude (S)-7-(1-(9H-purin-6-ylamino)ethyl)-6-(3-fluorophenyl)-3-methyl-5H-thiazolo[3,2-c]pyrimidin-5-one hydrochloride (Step 4, 1511 g) were charged to the solution and the resulting mixture was stirred at 25° C. for at least 30 min to afford an aqueous layer having pH greater than 9. The layers were allowed to separate, the organic layer was collected, and the aqueous layer was kept in the reactor. Additional DCM (2.0 L) was charged into the reactor and the resulting mixture was stirred for at least 10 min. The layers were allowed to separate and the organic layer was collected. The two organic extracts were combined, washed twice with water (2×5.0 L), and dried over anhydrous Na$_2$SO$_4$ (1000 g). The drying agent was filtered off and the filter cake was rinsed with DCM (3.0 L). The filtrate and wash were combined to afford crude (S)-7-(1-(9H-purin-6-ylamino)ethyl)-6-(3-fluorophenyl)-3-methyl-5H-thiazolo[3, 2-a]pyrimidin-5-one (15) as a solution in DCM, which was used directly in the next step.

Step 6. (S)-7-(1-(9H-Purin-6-ylamino)ethyl)-6-(3-fluorophenyl)-3-methyl-5H-thiazolo[3, 2-a]pyrimidin-5-one (Purified Product)

A clean and dry reactor equipped with an overhead stirrer, a thermocouple, a reflux condenser, an addition funnel, and a nitrogen inlet was purged with nitrogen and a nitrogen flow was maintained thereafter. The solution of the crude product in DCM (15a) was charged into the reactor through a 0.3 μm polish filter. The solution was concentrated under reduced pressure at below 30° C. to a minimum stirring volume (~5 L). EtOAc (5.0 L) was added and concentration was resumed under reduced pressure at below 40° C. to a minimum agitation volume (~5 L). Additional EtOAc (15 L) was added and the resulting mixture was heated at reflux for at least 1 h. The mixture was then cooled to 20° C. over a period of at least 3 h, and stirred at 20° C. for at least 2 h. The solids were collected via filtration, and the resulting filter cake was washed three times with EtOAc (3×1.0 L). The resulting wet cake was dried at below 50° C. under vacuum until the loss of drying was <0.5%, to afford (S)-7-(1-(9H-purin-6-ylamino)ethyl)-6-(3-fluorophenyl)-3-methyl-5H-thiazolo[3,2-a]pyrimidin-5-one (15, 1250 g, 90%) as a white solid. $^{1}$H NMR (400 MHz, CDCl$_3$) δ 14.15 (br s, 1H), 8.33 (s, 1H), 7.94 (s, 1H), 7.40 (m, 1H), 7.15-7.07 (m, 3H), 6.81 (d, J=8.4 Hz, 1H), 6.41 (d, J=1.2 Hz, 1H), 5.46 (br s, 1H), 2.74 (d, J=1.1 Hz, 3H), 1.42 (d, J=6.7 Hz, 3H); $^{13}$C NMR (100 MHz, CDCl$_3$) δ 163.9, 163.0 ($^{1}J_{CF}$=246.3 Hz), 162.3, 161.5, 153.8, 152.2, 149.9, 138.5, 137.0, 135.3 ($^{3}J_{CF}$=7.9 Hz), 130.2 ($^{3}J_{CF}$=8.4 Hz), 126.5 ($^{4}J_{CF}$=2.4 Hz), 119.7, 117.9 ($^{2}J_{CF}$=21.6 Hz), 116.5, 115.2 ($^{2}J_{CF}$=20.9 Hz), 106.4, 47.5, 21.1, 18.7; $^{19}$F NMR (376 MHz, CDCl$_3$) δ-113.3. LCMS calc. for C$_{20}$H$_{17}$FN$_7$OS (M+H)+: m/z 422.1. Found: 422.0.

Example A1. PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5) P3 Detector Protein, was purchased from Echelon Biosciences (Salt Lake City, Utah). AlphaScreen™ GST Detection Kit including donor and acceptor beads was purchased from PerkinElmer Life Sciences (Waltham, Mass.). PI3Kδ (p110δ/p85α) was purchased from Millipore (Bedford, Mass.). ATP, MgCl$_2$, DTT, EDTA, HEPES and CHAPS were purchased from Sigma-Aldrich (St. Louis, Mo.). AlphaScreen™ Assay for PI3Kδ

The kinase reaction was conducted in 384-well REMP plate from Thermo Fisher Scientific in a final volume of 40 μL. Inhibitors were first diluted serially in DMSO and added to the plate wells before the addition of other reaction components. The final concentration of DMSO in the assay was 2%. The PI3K assays were carried out at room temperature in 50 mM HEPES, pH 7.4, 5 mM MgCl$_2$, 50 mM NaCl, 5 mM DTT and CHAPS 0.04%. Reactions were initiated by the addition of ATP, the final reaction mixture consisted of 20 M PIP2, 20 M ATP, 1.2 nM PI3Kδ were incubated for 20 min. 10 μL of reaction mixture was then transferred to 5 μL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 μL AlphaScreen™ donor and acceptor beads suspended in quench buffer containing 25 nM PI(3,4,5)P3 detector protein. The final concentration of both donor and acceptor beads is 20 mg/ml. After plate sealing, the plate was incubated in a dark location at room temperature for 2 hours. The activity of the product was determined on Fusion-alpha microplate reader (Perkin-Elmer). IC$_{50}$ determination was performed by fitting the curve of percent control activity versus the log of the inhibitor concentration using the GraphPad Prism 3.0 software.

Example A2. PI3K Enzyme Assay

Materials

Lipid kinase substrate, phosphoinositol-4,5-bisphosphate (PIP2), was purchased from Echelon Biosciences (Salt Lake City, Utah). PI3K isoforms α, β, δ and γ were purchased from Millipore (Bedford, Mass.). ATP, MgCl$_2$, DTT, EDTA, MOPS and CHAPS were purchased from Sigma-Aldrich (St. Louis, Mo.).

The kinase reaction was conducted in clear-bottom 96-well plate from Thermo Fisher Scientific in a final volume of 24 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. The reaction mixture was prepared containing 50 μM PIP2, kinase and varying concentration of inhibitors. Reactions were initiated by the addition of ATP containing 2.2 μCi [γ-$^{33}$P]ATP to a final concentration of 1000 μM. The final concentration of PI3K isoforms α, β, δ and γ in the assay were 1.3, 9.4, 2.9 and 10.8 nM respectively. Reactions were incubated for 180 min and terminated by the addition of 100 μL of 1 M potassium phosphate pH 8.0, 30 mM EDTA quench buffer. A 100 μL aliquot of the reaction solution was then transferred to 96-well Millipore MultiScreen IP 0.45 μm PVDF filter plate (The filter plate was prewetted with 200 μL 100% ethanol, distilled water, and 1 M potassium phosphate pH 8.0, respectively). The filter plate was aspirated on a Millipore Manifold under vacuum and washed with 18×200 μL wash buffer containing 1 M potassium phosphate pH 8.0 and 1 mM ATP. After drying by aspiration and blotting, the plate was air dried in an incubator at 37° C. overnight. Packard TopCount adapter (Millipore) was then attached to the plate followed with addition of 120 μL Microscint 20 scintillation cocktail (Perkin Elmer) in each well. After the plate sealing, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. Compounds having and IC$_{50}$ value of 10 μM or less are considered active.

Example A3. PI3Kδ Scintillation Proximity Assay
Materials

[γ-$^{33}$P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p1106/p85a) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 20 μM ATP, 0.2 μCi [γ-$^{33}$P]ATP, 4 nM PI3Kδ. Reactions were incubated for 210 min and terminated by the addition of 40 μL SPA beads suspended in quench buffer: 150 mM potassium phosphate pH 8.0, 20% glycerol. 25 mM EDTA, 400 μM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software.

Example B1. B Cell Proliferation Assay

To acquire B cells, human PBMC were isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells were then purified by positive immunosorting using an autoMacs (Miltenyi Biotech) according to the manufacturer's instruction.

The purified B cells (2×10⁵/well/200 µL) were cultured in 96-well ultra-low binding plates (Corning, Corning, N.Y.) in RPMI1640, 10% FBS and goat F(ab')2 anti-human IgM (10 g/ml) (Invitrogen, Carlsbad, Calif.), in the presence of different amount of test compounds, for three days. [³H]-thymidine (1 µCi/well) (PerkinElmer, Boston, Mass.) in PBS was then added to the B cell cultures for an additional 12 hrs before the incorporated radioactivity was separated by filtration with water through GF/B filters (Packard Bioscience, Meriden, Conn.) and measured by liquid scintillation counting with a TopCount (Packard Bioscience). Compounds having and $IC_{50}$ value of 10 µM or less are considered active.

Example B2. Pfeiffer Cell Proliferation Assay

Pfeiffer cell line (diffuse large B cell lymphoma) was purchased from ATCC (Manassas, Va.) and maintained in the culture medium recommended (RPMI and 10% FBS). To measure the anti-proliferation activity of the PI3Kδ submittals, the Pfeiffer cells were plated with the culture medium (2×10³ cells/well/per 200 µl) into 96-well ultra-low binding plates (Corning, Corning, N.Y.), in the presence or absence of a concentration range of test compounds. After 3-4 days, [³H]-thymidine (1 µCi/well) (PerkinElmer, Boston, Mass.) in PBS was then added to the cell culture for an additional 12 hrs before the incorporated radioactivity was separated by filtration with water through GF/B filters (Packard Bioscience, Meridenj, Conn.) and measured by liquid scintillation counting with a TopCount (Packard Bioscience).

Example C. Akt Phosphorylation Assay

Ramos cells (B lymphocyte from Burkitts lymphoma) were obtained from ATCC (Manassas, Va.) and maintained in RPMI1640 and 10% FBS. The cells (3×10⁷ cells/tube/3 mL in RPMI) were incubated with different amounts of test compounds for 2 hrs at 37° C. and then stimulated with goat F(ab')2 anti-human IgM (5 g/mL) (Invitrogen) for 17 min. in a 37° C. water bath. The stimulated cells were spun down at 4° C. with centrifugation and whole cell extracts prepared using 300 µL lysis buffer (Cell Signaling Technology, Danvers, Mass.). The resulting lysates were sonicated and supernatants were collected. The phosphorylation level of Akt in the supernatants were analyzed by using PathScan phospho-Akt1 (Ser473) sandwich ELISA kits (Cell Signaling Technology) according to the manufacturer's instruction.

Example D: In Vitro JAK Kinase Assay

The compounds in Table A were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 µL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a PHERA star plate reader (BMG, Cary, N.C.). The data for the JAK1 and/or JAK2 inhibitors were obtained by testing the compounds in the Example D assay at 1 mM ATP.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A process, comprising reacting a compound of Formula (II):

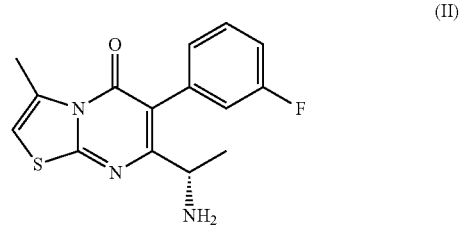 [SMILES: Cc1csc2nc([C@H](C)N)c(-c3cccc(F)c3)c(=O)n12]

with a compound of Formula (III):

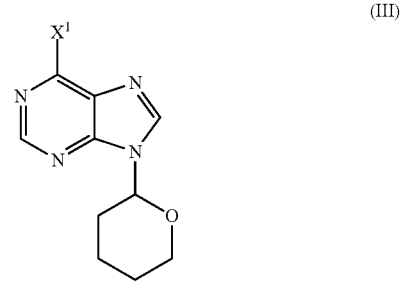

in the presence of a B1, wherein B1 is a base, to afford a compound of Formula (IV):

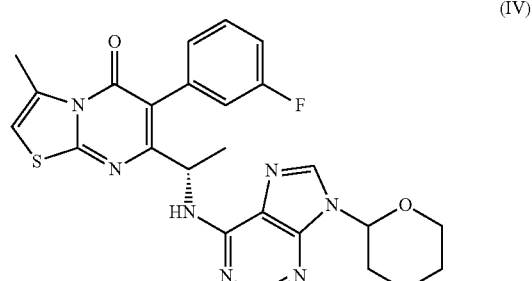

wherein $X^1$ is halo.

2. The process of claim 1, wherein $X^1$ is chloro.

3. The process of claim 1, wherein said B1 is an alkali metal bicarbonate base.

4. The process of claim 3, wherein said alkali metal bicarbonate base is sodium bicarbonate.

5. The process of claim 1, wherein said reacting is performed in a solvent comprising an alcohol.

6. The process of claim 5, wherein said alcohol is isopropanol.

7. The process of claim 1, wherein said reacting is performed at a temperature from 80° C. to 85° C.

8. The process of claim 1, wherein 1.1 to 1.5 equivalents of the compound of Formula (III) is used based on 1 equivalent of the compound of Formula (II).

9. The process of claim 1, further comprising deprotecting said compound of Formula (IV) in the presence of A1, wherein A1 is an acid, to afford a deprotected product which is a compound of Formula (I):

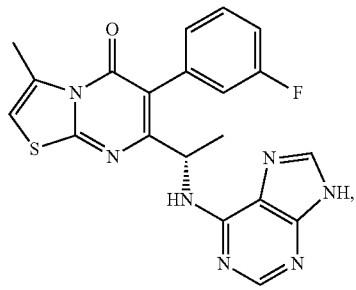

(I)

or a salt thereof.

10. The process of claim 9, wherein the deprotected product is a salt having Formula (Ia):

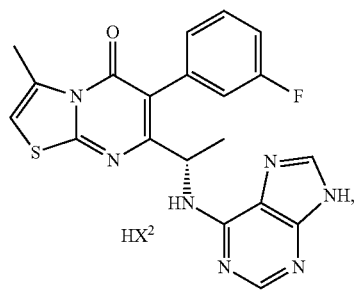

(Ia)

wherein $X^2$ is halide.

11. The process of claim 10, wherein $X^2$ is chloride.

12. The process of claim 9, wherein said A1 is an aqueous strong acid.

13. The process of claim 12, wherein said aqueous strong acid is aqueous hydrochloric acid.

14. The process of claim 9, wherein said deprotecting is performed in a solvent comprising an alcohol.

15. The process of claim 14, wherein said alcohol of said deprotecting step is isopropanol.

16. The process of claim 9, wherein said deprotecting is performed at a temperature from 25° C. to 35° C.

17. The process of claim 9, wherein 2.5 to 3.5 equivalents of A1 is used based on 1 equivalent of the compound of Formula (II).

18. The process of claim 9, wherein said reacting and deprotecting steps are conducted in the same pot without isolation of the compound of Formula (IV).

19. The process of claim 10, further comprising treating the salt of Formula (Ia) with B2, wherein B2 is a base, to form a compound of Formula (I):

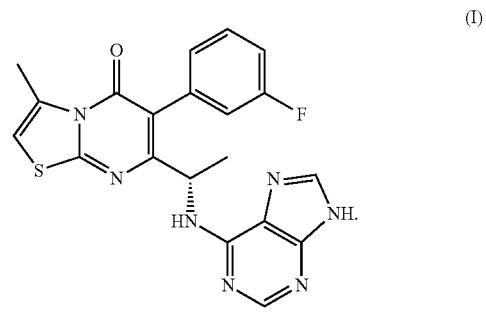 [SMILES: Cc1csc2nc([C@H](C)Nc3ncnc4[nH]cnc34)c(-c3cccc(F)c3)c(=O)n12]

(I)

20. The process of claim 19, wherein B2 is an alkali metal carbonate base.

21. The process of claim 20, wherein said alkali metal carbonate base is sodium carbonate.

22. The process of claim 19, wherein said treating is performed in a solvent comprising water and a halogenated solvent.

23. The process of claim 22, wherein said halogenated solvent is dichloromethane.

24. The process of claim 19, wherein 1.5 to 2.5 equivalents of B2 is used based on 1 equivalent of the salt of Formula (Ia).

25. The process of claim 19, wherein said treating is performed at room temperature.

26. The process of claim 1, wherein said compound of Formula (II) is prepared by:

(va) reacting a compound of Formula (V):

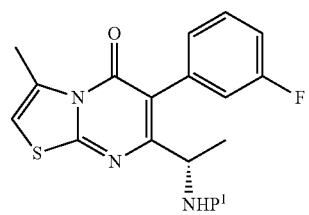

(V)

wherein $P^1$ is an amine protecting group, with A2, wherein A2 is an acid, followed by (vb) treating the product of the preceding step (va) with B3, wherein B3 is a base.

27. The process of claim 26, wherein said amine protecting group is tert-butoxycarbonyl.

28. The process of claim 26, wherein said A2 is hydrochloric acid.

29. The process of claim 26, wherein said compound of Formula (V) is prepared by a process comprising:
(iiia) reacting a complex of Formula (VI):

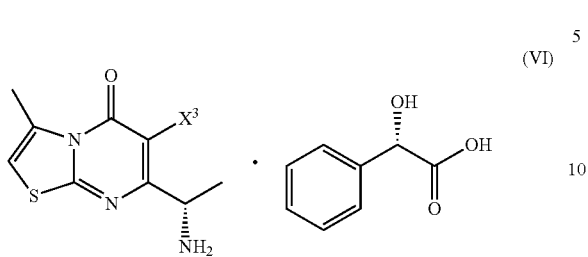

(VI)

wherein X³ is halo, with an amine protecting agent in the presence of B4, wherein B4 is a base, followed by:
(iiib) reacting the product of the preceding step (iiia) with (3-fluorophenyl)boronic acid in the presence of a transition metal catalyst.

30. The process of claim 29, wherein X³ is bromo.

31. The process of claim 29, wherein said amine protecting agent is di-tert-butyl dicarbonate.

32. The process of claim 29, wherein the transition metal catalyst is a palladium catalyst.

33. The process of claim 29, wherein said complex of Formula (VI) is prepared by reacting a compound of Formula (VII):

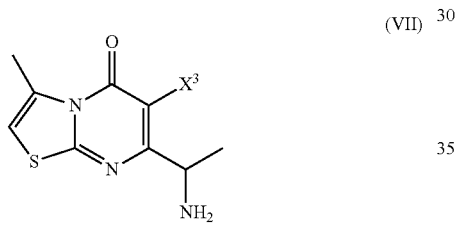

(VII)

with (S)-(+)-mandelic acid.

34. The process of claim 33, wherein X³ is bromo.

35. The process of claim 1, wherein the compound of Formula (III) is prepared by reacting a compound of Formula (VIII):

(VIII)

wherein X⁴ is halo, with 3,4-dihydro-2H-pyran in the presence of a A3, wherein A3 is an acid.

36. The process of claim 35, wherein X⁴ is chloro.

37. A process, comprising:
i) reacting a compound of Formula (IX):

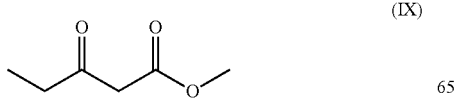

(IX)

with bromine to form a compound of Formula (Xa):

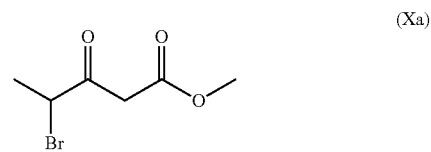

(Xa)

ii) reacting said compound of Formula (Xa) with 4-methylthiazol-2-amine in the presence of polyphosphoric acid to form a compound of Formula (XIa):

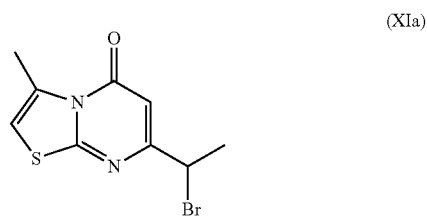

(XIa)

iii) reacting said compound of Formula (XIa) with N-bromosuccinimide to form a compound of Formula (XIIa):

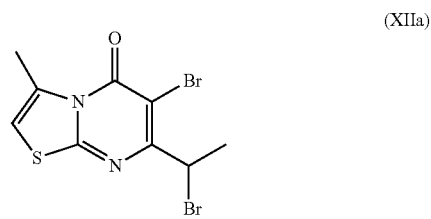

(XIIa)

iv) reacting said compound of Formula (XIIa) with sodium azide to form a compound of Formula (XIIIa):

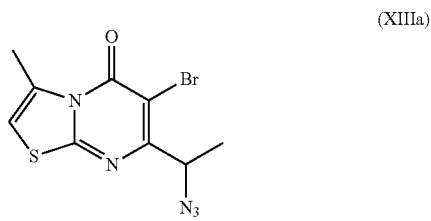 [SMILES: Cc1csc2nc(C(C)N=[N+]=[N-])c(Br)c(=O)n12]

(XIIIa)

v) reacting said compound of Formula (XIIIa) with TMS-Cl in the presence of sodium iodide to form a compound of Formula (VIIa):

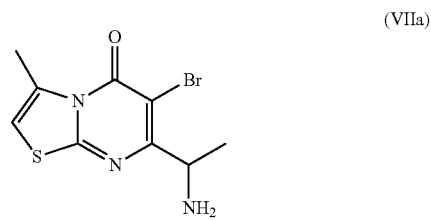

(VIIa)

vi) reacting said compound of Formula (VIIa) with (S)-(+)-mandelic acid to form a compound of Formula (VIa):

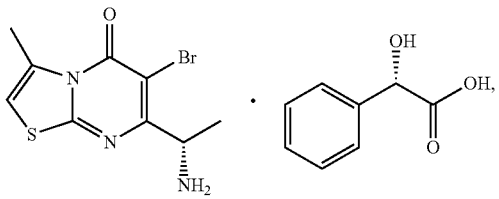

(VIa)

vii) protecting said compound of Formula (VIa) with di-tert-butyl dicarbonate in the presence of sodium carbonate;

viii) reacting the product of step vii) with (3-fluorophenyl)boronic acid in the presence of dichloro(bis{di-tert-butyl[4-(dimethylamino)phenyl]-phosphoranyl})palladium (Pd-132) to form a compound of Formula (Va):

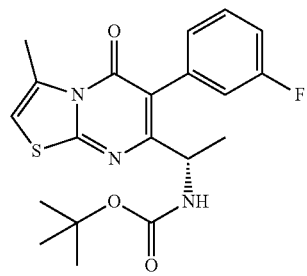

(Va)

ix) reacting said compound of Formula (Va) with hydrochloric acid;

x) reacting the product of step ix) with sodium carbonate to form a compound of Formula (II):

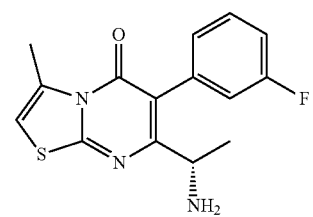

(II)

xi) reacting said compound of Formula (II) with a compound of Formula (IIIa):

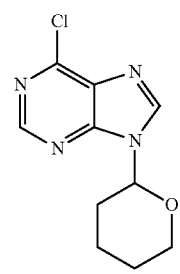

(IIIa)

in the presence of sodium carbonate to afford a compound of Formula (IV):

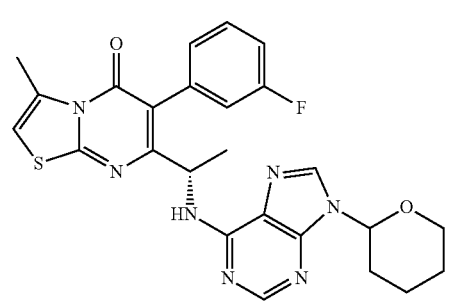

(IVa)

xii) deprotecting said compound of Formula (IVa) in the presence of hydrochloric acid to form a salt of Formula (Ib):

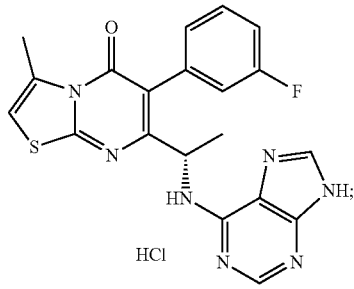

(Ib)

and xiii) reacting said salt of Formula (Ib) with sodium carbonate to form a compound of Formula (I):

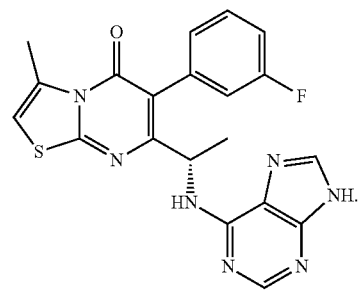

(I)

38. A process, comprising:

i) reacting a compound of Formula (VIIa)

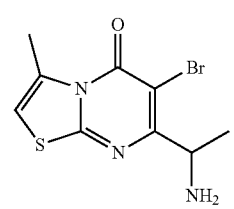

(VIIa)

with (S)-(+)-mandelic acid to form a compound of Formula (VIa)

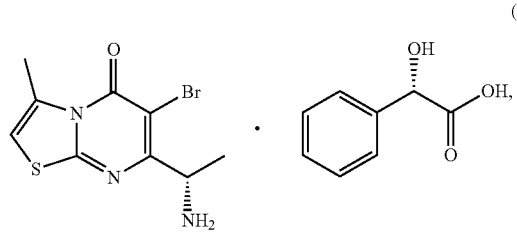

ii) protecting said compound of Formula (VIa) with di-tert-butyl dicarbonate in the presence of sodium carbonate;
iii) reacting the product of step ii) with (3-fluorophenyl) boronic acid in the presence of dichloro(bis{di-tert-butyl[4-(dimethylamino)phenyl]-phosphoranyl})palladium (Pd-132) to form a compound of Formula (Va):

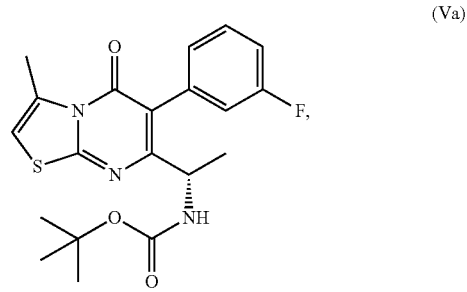 [SMILES: Cc1csc2nc([C@H](C)NC(=O)OC(C)(C)C)c(-c3cccc(F)c3)c(=O)n12]

iv) reacting said compound of Formula (Va) with hydrochloric acid;
v) reacting the product of step iv) with sodium carbonate to form a compound of Formula (II):

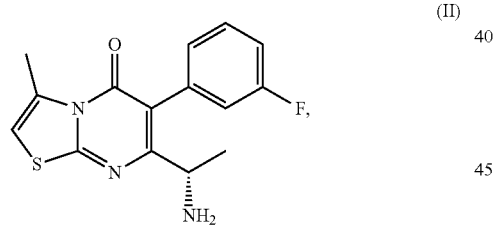

vi) reacting said compound of Formula (II) with a compound of Formula (Ma):

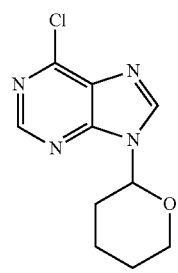

in the presence of sodium carbonate to afford a compound of Formula (IV):

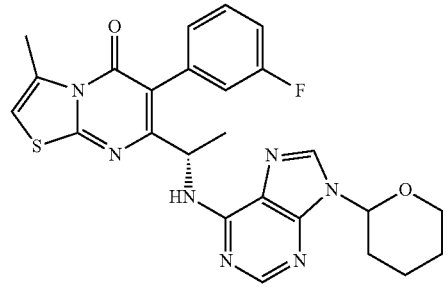

vii) deprotecting said compound of Formula (IV) in the presence of hydrochloric acid to form a salt of Formula (Ib):

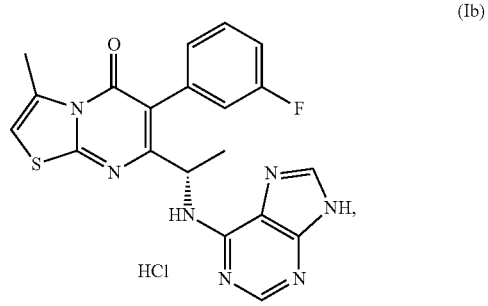 [SMILES: Cc1csc2nc([C@H](C)Nc3ncnc4[nH]cnc34)c(-c3cccc(F)c3)c(=O)n12 ; Cl]

viii) reacting said salt of Formula (Ib) with sodium carbonate to form a compound of Formula (I):

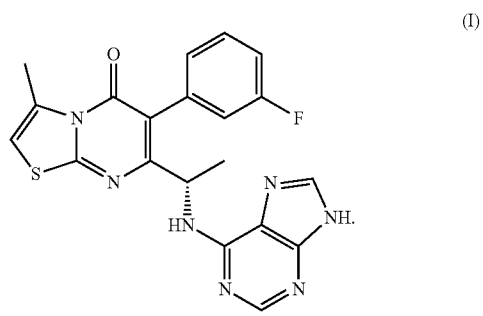 [SMILES: Cc1csc2nc([C@H](C)Nc3ncnc4[nH]cnc34)c(-c3cccc(F)c3)c(=O)n12]

39. A compound of Formula (IV):

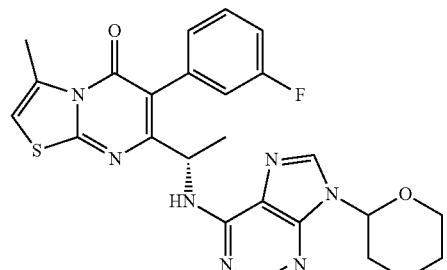

or a salt thereof.

* * * * *